United States Patent
Beccati et al.

(10) Patent No.: US 8,435,795 B2
(45) Date of Patent: May 7, 2013

(54) EVALUATING HEPARIN PREPARATIONS

(75) Inventors: Daniela Beccati, Watertown, MA (US); Ishan Capila, Ashland, MA (US); Nur Sibel Gunay, Chestnut Hill, MA (US); Sucharita Roy, Tyngsboro, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 2 days.

(21) Appl. No.: 13/008,442

(22) Filed: Jan. 18, 2011

(65) Prior Publication Data
US 2011/0207919 A1 Aug. 25, 2011

Related U.S. Application Data

(60) Provisional application No. 61/296,218, filed on Jan. 19, 2010, provisional application No. 61/347,950, filed on May 25, 2010.

(51) Int. Cl.
C08B 37/10 (2006.01)
G01N 33/00 (2006.01)
G01R 33/44 (2006.01)

(52) U.S. Cl.
USPC ............. 436/94; 436/161; 436/173; 210/656; 250/282; 536/21; 73/61.52; 324/307; 204/451

(58) Field of Classification Search ............... 436/94, 436/161, 173, 174; 210/656; 250/281, 282; 536/21; 73/61.43, 61.52; 324/307; 204/451
See application file for complete search history.

(56) References Cited

U.S. PATENT DOCUMENTS

| | | | |
|---|---|---|---|
| 3,832,253 A | 8/1974 | DiPalma |
| 3,854,480 A | 12/1974 | Zaffaroni |
| 4,452,775 A | 6/1984 | Kent |
| 4,652,555 A | 3/1987 | Goulay et al. |
| 4,667,014 A | 5/1987 | Nestor, Jr. et al. |
| 4,686,288 A | 8/1987 | Lormeau et al. |
| 4,687,765 A | 8/1987 | Vairel et al. |
| 4,692,435 A | 9/1987 | Lormeau et al. |
| 4,748,034 A | 5/1988 | de Rham |
| 4,791,195 A | 12/1988 | Bianchini et al. |
| 4,826,827 A | 5/1989 | Lormeau et al. |
| 4,847,338 A | 7/1989 | Linhardt et al. |
| 4,916,219 A | 4/1990 | Linhardt et al. |
| 4,933,326 A | 6/1990 | Bianchini et al. |
| 4,977,250 A | 12/1990 | Diaz et al. |

(Continued)

FOREIGN PATENT DOCUMENTS

| EP | 121067 B1 | 10/1984 |
|---|---|---|
| EP | 244235 B1 | 11/1987 |

(Continued)

OTHER PUBLICATIONS

International Search Report and Written Opinion from International Application Serial No. PCT/US11/21582 mailed Mar. 21, 2011.

(Continued)

*Primary Examiner* — Maureen Wallenhorst
(74) *Attorney, Agent, or Firm* — Lando & Anastasi, LLP

(57) ABSTRACT

Methods of evaluating heparin preparations, e.g., for suitability for use as a drug or for use in making a drug, by determining the absence, presence or amount of a structural signature that is indicative of the methods used to make the heparin preparation.

15 Claims, 17 Drawing Sheets

U.S. PATENT DOCUMENTS

| | | | |
|---|---|---|---|
| 4,981,955 A | 1/1991 | Lopez | |
| 4,990,502 A | 2/1991 | Lormeau et al. | |
| 5,010,063 A | 4/1991 | Piani et al. | |
| 5,013,724 A | 5/1991 | Petitou et al. | |
| 5,013,725 A | 5/1991 | Isomura et al. | |
| 5,019,649 A | 5/1991 | Lormeau et al. | |
| 5,032,679 A | 7/1991 | Brandley et al. | |
| 5,039,529 A | 8/1991 | Bergendal et al. | |
| 5,084,564 A | 1/1992 | Vila et al. | |
| 5,104,860 A | 4/1992 | Piani et al. | |
| 5,106,734 A | 4/1992 | Nielsen | |
| 5,110,918 A | 5/1992 | Casu et al. | |
| 5,164,378 A | 11/1992 | Conti et al. | |
| 5,239,660 A | 8/1993 | Ooi | |
| 5,264,425 A | 11/1993 | Dal Pozzo et al. | |
| 5,296,471 A | 3/1994 | Holme et al. | |
| 5,340,932 A | 8/1994 | Fussi et al. | |
| 5,380,716 A | 1/1995 | Conrad et al. | |
| 5,389,618 A | 2/1995 | Debrie | |
| 5,403,827 A | 4/1995 | De-Ambrosi | |
| 5,410,039 A | 4/1995 | Ungarelli et al. | |
| 5,430,132 A | 7/1995 | Silvano et al. | |
| 5,430,133 A | 7/1995 | Piani et al. | |
| 5,599,801 A | 2/1997 | Branellec et al. | |
| 5,668,118 A | 9/1997 | Kennedy | |
| 5,696,100 A | 12/1997 | Holme et al. | |
| 5,707,973 A | 1/1998 | Baron et al. | |
| 5,707,974 A | 1/1998 | Kennedy | |
| 5,721,973 A | 2/1998 | Mizukawa | |
| 5,763,421 A | 6/1998 | Caretto et al. | |
| 5,767,269 A | 6/1998 | Hirsh et al. | |
| 5,783,570 A | 7/1998 | Yokota et al. | |
| 5,808,021 A | 9/1998 | Holme et al. | |
| 5,849,721 A | 12/1998 | Uzan | |
| 5,912,237 A | 6/1999 | Kennedy | |
| 5,922,358 A | 7/1999 | Doutremepuich et al. | |
| 5,935,850 A | 8/1999 | Clark et al. | |
| 5,958,899 A | 9/1999 | Zoppetti et al. | |
| 6,045,805 A | 4/2000 | Moreau | |
| 6,075,013 A | 6/2000 | Weitz et al. | |
| 6,077,683 A | 6/2000 | Kennedy | |
| 6,143,730 A | 11/2000 | Parish et al. | |
| 6,197,943 B1 | 3/2001 | Casu et al. | |
| 6,217,863 B1 | 4/2001 | Godavarti et al. | |
| 6,228,998 B1 | 5/2001 | Miura et al. | |
| 6,232,093 B1 | 5/2001 | Van Houdenhoven et al. | |
| 6,255,296 B1 | 7/2001 | Daniels | |
| 6,258,798 B1 | 7/2001 | Wallentin | |
| 6,346,517 B1 | 2/2002 | Wong et al. | |
| 6,384,021 B1 | 5/2002 | Mardiguian | |
| 6,492,503 B1 | 12/2002 | Kariya et al. | |
| 6,617,316 B1 | 9/2003 | Mourier et al. | |
| 6,812,221 B2 | 11/2004 | McKeehan et al. | |
| RE38,743 E | 6/2005 | Debrie | |
| 7,008,933 B2 | 3/2006 | Welzel | |
| 7,083,937 B2 | 8/2006 | Sasisekharan et al. | |
| 7,390,633 B2 | 6/2008 | Liu et al. | |
| 7,575,886 B2 * | 8/2009 | Venkataraman et al. | 435/18 |
| 7,585,642 B2 * | 9/2009 | Sasisekharan et al. | 435/13 |
| 7,687,579 B2 | 3/2010 | Takahashi et al. | |
| 7,790,466 B1 | 9/2010 | Shriver et al. | |
| 7,811,827 B2 | 10/2010 | Raguram | |
| 7,816,144 B1 | 10/2010 | Shriver et al. | |
| 7,968,082 B1 * | 6/2011 | Shriver et al. | 424/9.3 |
| 8,003,402 B2 | 8/2011 | Yamamoto et al. | |
| 8,076,149 B1 | 12/2011 | Shriver et al. | |
| 8,101,733 B1 | 1/2012 | Shriver et al. | |
| 2002/0169143 A1 | 11/2002 | Sasisekharan et al. | |
| 2003/0203385 A1 | 10/2003 | Venkataraman et al. | |
| 2004/0198697 A1 | 10/2004 | Cohen et al. | |
| 2004/0265943 A1 | 12/2004 | Viskov et al. | |
| 2005/0119477 A1 | 6/2005 | Mourier et al. | |
| 2005/0186679 A1 | 8/2005 | Viskov et al. | |
| 2005/0215519 A1 | 9/2005 | Viskov et al. | |
| 2005/0288252 A1 | 12/2005 | Nurcombe et al. | |
| 2006/0024664 A1 | 2/2006 | Sasisekharan et al. | |
| 2006/0182734 A1 | 8/2006 | Liu et al. | |
| 2007/0065921 A1 | 3/2007 | Sasisekharan et al. | |
| 2007/0098708 A1 | 5/2007 | Myette | |
| 2007/0134226 A1 | 6/2007 | Myette | |
| 2007/0161073 A1 | 7/2007 | Sasisekharan et al. | |
| 2007/0287683 A1 * | 12/2007 | Shriver et al. | 514/56 |
| 2008/0009069 A1 | 1/2008 | Mourier et al. | |
| 2008/0318328 A1 | 12/2008 | Viskov et al. | |
| 2010/0279269 A1 * | 11/2010 | Parsons et al. | 435/4 |
| 2011/0207919 A1 | 8/2011 | Beccati et al. | |

FOREIGN PATENT DOCUMENTS

| | | |
|---|---|---|
| EP | 244236 A2 | 11/1987 |
| EP | 245813 B1 | 11/1987 |
| EP | 268885 B1 | 6/1988 |
| EP | 293539 A2 | 12/1988 |
| EP | 302034 B1 | 2/1989 |
| EP | 319559 A1 | 6/1989 |
| EP | 347588 B1 | 12/1989 |
| EP | 423151 B1 | 9/1993 |
| EP | 380943 B1 | 9/1994 |
| EP | 432537 B1 | 1/1995 |
| EP | 483733 B1 | 8/1996 |
| EP | 623629 B1 | 8/1996 |
| EP | 625166 B1 | 9/1997 |
| EP | 557887 B1 | 12/1997 |
| EP | 708785 B1 | 3/1999 |
| EP | 693499 B1 | 12/1999 |
| EP | 789777 B1 | 8/2000 |
| EP | 970130 B1 | 7/2002 |
| EP | 735050 B1 | 9/2002 |
| EP | 1580197 A1 | 9/2005 |
| EP | 1582531 A1 | 10/2005 |
| EP | 1586588 A1 | 10/2005 |
| JP | 11230935 A | 8/1999 |
| WO | 8809347 A1 | 12/1988 |
| WO | 9003791 A1 | 4/1990 |
| WO | 9914326 A1 | 3/1999 |
| WO | 0065521 A2 | 11/2000 |
| WO | 0129055 A2 | 4/2001 |
| WO | 0223190 A2 | 3/2002 |
| WO | 0232406 A2 | 4/2002 |
| WO | 03078960 A2 | 9/2003 |
| WO | 2004027087 A2 | 4/2004 |
| WO | 2005009040 A2 | 1/2005 |
| WO | 2005080438 A1 | 9/2005 |
| WO | 2005090411 A1 | 9/2005 |

OTHER PUBLICATIONS

Lindhart et al., "New methodologies in heparin structure analysis and the genereation of LMW heparins", Heparin and Related Polysaccharides, 1992, pp. 37-47, ed. D.A. Lane et al., Plenum Press, New York.

Lindhart et al., "Oligosaccharide mapping of low molecular weight heparins: structure and activity differences", J. of Medicinal Chem., 1990, vol. 33, No. 6, pp. 1639-1645.

Liotta et al., "Cancer metastasis and angiogenesis: an imbalance of positive and negative regulation", Cell, 1991, vol. 64, pp. 327-336.

Liu et al., "A heparin-binding synthetic peptide of heparin/heparan sulfate-interacting protein modulates blood coagulation activities", PNAS, 1997, vol. 94, pp. 1739-1744.

Liu et al., "Strategy for the sequence analysis of heparin", Glycobiology, 1995, vol. 5, pp. 765-774.

Lou et al., "Structural Specificity in a FGF7-Affinity Purified Heparin Octasaccharide Required for Formation of a Complex with FGF7 and FGFR2IIIb" Journal of Cellular Biochemistry, vol. 97, pp. 1241-1258 (2006).

Lupetti et al., "Translation of a retained intron in tyrosinase-related protein (TRP) 2 mRNA generates a new cytotoxic T lymphocyte (CTL)-defined and shared human melanoma antigen not expressed in normal cells of the melanocytic lineage", J. Exp. Med., 1998, vol. 188, pp. 1005-1016.

Malsch et al., "High-resolution capillary electrophoresis and polyacrylamide gel electrophoresis of heparins," Journal of Chromatography A, 1995, vol. 716, pp. 258-268.

Mandruzzato et al., "A CASP-8 mutation recognized by cytolytic T lymphocytes on a human head and neck carcinoma", J. Exp. Med., 1997, vol. 186, pp. 785-793.

Manici et al., "Melanoma cells present a MAGE-3 epitope to CD4(+) cytotoxic T cells in association with histocompatibility leukocyte antigen DR11", J. Exp. Med., 1999, vol. 189, pp. 871-876.

Mascellani et al., "Characterization of di- and monosulfated, unsaturated heparin disaccharides with terminal N-sulfated 1,6-anhydro-b-D-glucosamine or N-sulfated 1,6-anydro-b-D-mannosamine residues", Carbohydrate Research, 2007, vol. 342, pp. 835-842.

Mauray et al., "Mechanism of factor IXa inhibition by antithrombin in the presence of unfractionated and low molecular weight heparins and fucoidan", Biochim. Biophys. Acta, vol. 1387, No. 1-2, pp. 184-194, (1998).

McLaurin et al., "Interactions of Alzheimer amyloid-b peptides with glycosaminoglycans effects on fibril nucleation and growth", Eur. J. Biochem., 1999, vol. 266, pp. 1101-1110.

Merchant et al., "Structure of heparin-derived tetrasaccharides", Biochem. Journal, 1985, vol. 229, pp. 369-377.

Merry et al., "Highly sensitive sequencing of the sulfated domains of heparan sulfate", J. Biol. Chem., 1999, vol. 274, pp. 18455-18462.

Militsopoulou et al., "Determination of twelve heparin- and heparan sulfate-derived disaccharides as 2-aminoacridone derivatives by capillary zone electrophoresis using ultrviolet and laser-induced flourescence detection", Electrophoresis, 2002, vol. 23, pp. 1104-1109.

Morel et al., "A tyrosinase peptide presented by HLA-B35 is recognized on a human melanoma by autologous cytotoxic T lymphocytes", Int. J. Cancer, 1999, vol. 83, pp. 755-759.

Morell et al., "Analysis of starch structure using fluorophore-assisted carbohydrate electrophoresis", Electrophoresis, 1998, vol. 19, No. 15, pp. 2603-2611.

Oiso et al., "A newly identified MAGE-3-derived epitope recognized by HLA-A24-restricted cytotoxic T lymphocytes", Int. J. Cancer, 1999, vol. 81, pp. 387-394.

Parish et al., "A basement-membrane permeability assay which correlates with the metastatic potential of tumour cells", Int. J. Cancer, 1992, vol. 52, pp. 378-383.

Park et al., "Purification and characterization of heparin sulphate proteoglycan from bovine brain", Biochem. Journal, 1999, vol. 344, pp. 723-730.

Parkhurst et al., "Identification of a shared HLA-A*0201-restricted T-cell epitope from the melanoma antigen tyrosinase-related protein 2 (TRP2)", Cancer Research, 1998, vol. 58, pp. 4895-4901.

Perlin et al., "Spectroscopic methods", The Polysaccharides, 1982, vol. 1, pp. 133-193, Edited by G.O., Academic Press.

Pervin et al., "Separation of glycosaminoglycan-derived oligosaccharides by capillary electrophoresis using reverse polarity", Analytical Biochem., 1994, vol. 221, pp. 182-188.

Petitou et al., "Synthetic oligosaccharides having various functional domains: potent and potentially safe heparin mimetics", Bioorg. Med. Chem. Lett., 1999, vol. 9, No. 8, pp. 1161-1166.

Piani et al., "Alkali-induced optical rotation changes in heparins and heparan sulfates, and their relation to iduronic acid-containing sequences", Journal of Carbohydrate Chemistry, 1993, vol. 12, No. 4&5, pp. 507-521.

Pieper et al., "Biochemical identification of a mutated human melanoma antigen recognized by CD4(+) T cells", J. Exp. Med., 1999, vol. 189, pp. 757-765.

Pojasek, et al., "Histidine 295 and histidine 510 are crucial for the enzymatic degradation of heparan sulfate by heparinase III", Biochemistry, 2000, vol. 39, pp. 4012-4019.

Razi et al., "Structural and functional properties of heparin analogues obtained by chemical sulphation of *Escherichia coli* K5 capsular polysaccharide", Biochem. J., vol. 309, No. 2, pp. 465-475, 1995.

Rhomberg et al., "Mass spectrometric and capillary electrophoretic investigation of the enzymatic degradation of heparin-like glycosaminoglycans", PNAS, 1998, vol. 95, pp. 4167-4181.

Rhomburg et al., "Mass spectrometric evidence for the enzymatic mechanism of the depolymerization of heparin-like like glycosaminoglycans by heparinase II", PNAS USA, 1998, vol. 95, pp. 12232-12237.

Rice et al., "Gradient page and strong anion exchange Sax Hplc as analytical tools for sequencing the heparin polymer", American Chemical Society, 1987, vol. 193, pp. 1, Abstracts of paper from the National Meeting.

Rice et al., "High-performance liquid chromatographic separation of heparin-derived oligosaccharides", Analytical Biochem., 1985, vol. 150, No. 2, pp. 325-331.

Robbins et al., "A mutated b-catenin gene encodes a melanoma-specific antigen recognized by tumor infiltrating lymphocytes", J. Exp. Med., 1996, vol. 183, pp. 1185-1192.

Robbins et al., "The intronic region of an incompletely spliced gp100 gene transcript encodes an epitope recognized by melanoma-reactive tumor-infiltrating lymphocytes", J. Immunol., 1997, vol. 159, pp. 303-308.

Ronsin et al., "A non-AUG-defined alternative open reading frame of the intestinal carboxyl esterase mRNA generates an epitope recognized by renal cell carcinoma-reactive tumor-infiltrating lymphocytes in situ", J. Immunol., 1999, vol. 163, pp. 483-490.

Rota et al., "Free radical generation during chemical depolymerization of heparin", Analytical Biochemistry, vol. 344, pp. 193-203 (2005).

Ruiz-Calero et al., "Pressure-assisted capillary electrophoresis-electrospray ion trap mass spectrometry for the analysis of heparin depolymerised disaccharides", J. of Chromatogrphy A, 2001, vol. 914, pp. 277-291.

Ruiz-Calero et al., "Use of reversed polarity and pressure gradient in the analysis of disaccharide composition of heparin by capillary electrophoresis", J. of Chromatography A, 1998, vol. 828, pp. 497-508.

Röpke et al., "Spontaneous human squamous cell carcinomas are killed by a human cytotoxic T lymphocyte clone recognizing a wild-type p53-derived peptide", Proc. Natl. Acad. Sci. USA, 1996, vol. 93, pp. 14704-14707.

Saad et al., "Compositional analysis and quantification of heparin and heparan sulfate by electrospray ionization ion trap mass spectrometry", Anal. Chem., 2003, vol. 75, pp. 2985-2995.

Sasisekharan et al. "Heparinase inhibits neovascularization", Proc. Natl. Acad. Sci. USA, 1994, vol. 91, pp. 1524-1528.

Scapol et al., "Capillary electrophoresis of heparin and dermatan sulfate unsaturated disaccharides with triethylamine and acetonitrile as electrolyte additives", J. of Chromatography A, 1996, vol. 735, pp. 367-374.

Schanda, "Very fast two-dimensional NMR spectroscopy for real-time investigation of dynamic events in proteins on the time scale of seconds", Journal of the American Chemical Society, 2005, vol. 127, pp. 8014-8015.

Schneider et al., "Overlapping peptides of melanocyte differentiation antigen Melan-A/MART-1 recognized by autologous cytolytic T lymphocytes in association with HLA-B45.1 and HLA-A2.1", Int. J. Cancer, 1998, vol. 75, pp. 451-458.

Shriver et al., "Cleavage of the antithrombin III binding site in heparin by heparinases and its implication in the generation of low molecular weight heparin", PNAS, 2000, vol. 97, No. 19, pp. 10365-10370.

Shriver et al., "Sequencing of 3-0 sulfate containing heparin decasaccharides with a partial antithrombin III binding site", PNAS, 2000, vol. 97, No. 19, pp. 10359-10364.

Skipper et al., "An HLA-A2-restricted tyrosinase antigen on melanoma cells results from posttranslational modification and suggests a novel pathway for processing of membrane proteins", J. Exp. Med., 1996, vol. 183, pp. 527-534.

Skipper et al., "Shared epitopes for HLA-A3-restricted melanoma-reactive human CTL include a naturally processed epitope from Pmel-17/gp100", J. Immunol., 1996, vol. 157, pp. 5027-5033.

Sudor et al., "End-label free-solution electrophoresis of the low molecular weight heparins", Anal. Chem., 1997, vol. 69, No. 16, pp. 3199-3204.

Sundaram et al., "Rational design of low-molecular weight heparins with improved in vivo activity," PNAS, Jan. 21, 2003, vol. 100, No. 2, pp. 651-656.

Supplemental Partial European Search Report from European Application No. EP 037446289 dated Jul. 14, 2008.

Tahara et al., "Identification of a MAGE-2-encoded human leukocyte antigen-A24-binding synthetic peptide that induces specific antitumor cytotoxic T lymphocytes", Clin. Cancer Res., 1999, vol. 5, pp. 2236-2241.

Tanaka et al., "Induction of antitumor cytotoxic T lymphocytes with a MAGE-3-encoded synthetic peptide presented by human leukocytes antigen-A24", Cancer Res., 1997, vol. 57, pp. 4465-4468.

Tanzarella et al., "Identification of a promiscuous T-cell epitope encoded by multiple members of the MAGE family", Cancer Res., 1999, vol. 59, pp. 2668-2674.

Thanawiroon et al., "Liquid chromatography/mass spectrometry sequencing approach for highly sulfated heparin-derived oligosaccharides", J. of Biological Chem., 2004, vol. 279, No. 4, pp. 2608-2615.

Thanawiroon et al., "Separation of a complex mixture of heparin-derived oligosaccharides using reversed-phase high-performance liquid chromatography", J. of Chromatography A, 2003, vol. 1014, pp. 215-223.

Toida et al., "Structural differences and the presence of unsubstituted amino groups in heparan sulphates from different tissues and species", Biochem. Journal, 1997, vol. 322, pp. 499-506.

Topalian et al., "Melanoma-specific CD4+ T cells recognize nonmutated HLA-DR-restricted tyrosinase epitopes", J. Exp. Med., 1996, vol. 183, pp. 1965-1971.

Toyoda et al., "Rapid and sensitive analysis of disaccharide composition in heparin and heparan sulfate by reversed-phase ion-pair chromatography on a 2 mm porous silica gel column", J. of Chromatography A, 1999, vol. 830, pp. 197-201.

Traversari et al., "A nonapeptide encoded by human gene MAGE-1 is recognized on HLA-A1 by cytolytic T lymphocytes directed against tumor antigen MZ2-E", J. Exp. Med., 1992, vol. 176, pp. 1453-1457.

Trehy et al., "Analysis of heparin sodium by SAX/HPLC for contaminants and impurities", Journal of Pharmaceutical and Biomedical Analysis, 2009, vol. 49, No. 3, pp. 671-673.

Tsai et al., "Identification of subdominant CTL epitopes of the GP100 melanoma-associated tumor antigen by primary in vitro immunization with peptide-pulsed dendritic cells", J. Immunol., 1997, vol. 158, pp. 1796-1802.

Tsang et al., "Generation of human cytotoxic T cells specific for human carcinoembryonic antigen epitopes from patients immunized with recombinant vaccinia-CEA vaccine", J. Natl. Cancer Inst., 1995, vol. 87, pp. 982-990.

Tsuda et al., "The cell-surface proteoglycan Dally regulates Wingless signalling in *Drosophila*", Nature, 1999, vol. 400, pp. 276-280.

Turnbull et al., "A strategy for rapid sequencing of heparan sulfate and heparin saccharides", Proc. Natl. Acad. Sci. USA, 1999, vol. 96, pp. 2698-2703.

Van Den Eynde et al., "A new family of genes coding for an antigen recognized by autologous cytolytic T lymphocytes on a human melanoma", J. Exp. Med., 1995, vol. 182, pp. 689-698.

Van Der Bruggen et al., "A peptide encoded by human gene MAGE-3 and presented by HLA-A2 induces cytolytic T lymphocytes that recognize tumor cells expressing MAGE-3", Eur. J. Immunol., 1994, vol. 24, pp. 3038-3043.

Van Der Bruggen et al., "Autologous cytolytic T lymphocytes recognize a MAGE-1 nonapeptide on melanomas expressing HLA-Cw*1601", Eur. J. Immunol., vol. 24, pp. 2134-2140, 1994.

Van Putten et al., Determination of low molecular weight heparin in clinical laboratory, Haemostasis, 1984, vol. 14, pp. 205-210.

Venkataraman et al., "Sequencing complex polysaccharides", Science, 1999, vol. 286, pp. 537-542.

Volpi et al., "Characterization of heparins with different relative molecular masses (from 11 600 to 1600) by various analytical techniques", J. of Chromatography, 1993, vol. 622, pp. 13-20.

Volpi et al., "Hyaluronic acid and chondroitin sulfate unsaturated disaccharides analysis by high-performance liquid chromatography and fluorimetric detection with dansylhydrazine", Analytical Biochem., 2002, vol. 277, pp. 19-24.

Vonderheide et al., "The telomerase catalytic subunit is a widely expressed tumor-associated antigen recognized by cytotoxic T lymphocytes", Immunity, 1999, vol. 10, pp. 673-679.

Vynios et al., "Advances in analysis of glycosaminoglycans: its applications for the assessment of physiological and pathological states of connective tissues", J. of Chromatography B, 2002, vol. 781, pp. 21-38.

Wang et al. "Cloning genes encoding MHC Claa II-restricted antigens: mutated CDC27 as a tumor antigen", Science, 1999, vol. 284, pp. 1351-1354.

Wang et al., "A breast and melanoma-shared tumor antigen: T cell response to antigenic peptides translated from different open reading frames", J. Immunol., 1998, vol. 161, pp. 3596-3606.

Wang et al., "Identification of TRP-2 as a human tumor antigen recognized by cytotoxic T lymphocytes", J. Exp. Med., 1996, vol. 184, pp. 2207-2216.

Wang et al., "Utilization of an alternative open reading frame of a normal gene in generating a novel human cancer antigen", J. Exp. Med., 1996, vol. 183, pp. 1131-1140.

Watt et al., "Comparison of ovine, bovine and porcine mucosal heparins and low molecular weight heparins by disaccharide analyses and 13C NMR", Carbohydrate Polymers, 1997, vol. 33, pp. 5-11.

Wölfel et al., "A p16INK4a-insensitive CDK4 mutant targeted by cytolytic T lymphocytes in a human melanoma", Science, 1995, vol. 269, pp. 1281-1284.

Wölfel et al., "Two tyrosinase nonapeptides recognized on HLA-A2 melanomas by autologous cytolytic T lymphocytes", Eur. J. Immunol., 1994, vol. 24, pp. 759-764.

Yates et al., "1H and 13C NMR spectral assignments of the major sequences of twelve systematically modified heparin derivatives", Carbohydrate Research, 1996, vol. 294, pp. 15-27.

Yoshida et al., "Analyisis of unsaturated disaccharides from glycosaminoglycuronan by high-performance liquid chromatography", Analytical Biochem., 1989, vol. 117, pp. 327-332.

Zorn et al., "A MAGE-6-encoded peptide is recognized by expanded lymphocytes infiltrating a spontaneously regressing human primary melanoma lesion", Eur. J. Immunol., 1999, vol. 29, pp. 602-607.

"2.6.26. Test for anti-D antibodies in intravenous immunglobulin", Pharmeuropa, Jan. 2004, vol. 16, No. 1, pp. 121-122.

Aarnoudse et al., "Interleukin-2-induced, melanoma-specific T cells recognize CAMEL, an unexpected translation product of LAGE-1" Int. J. Cancer, 1999, vol. 82, pp. 442-448.

Alban et al., "Development of SPC-ELISA: a new assay principle for the study of sulfated polysaccharide-protein interactions", Journal of Biomolecular Screening, 2001, vol. 6, No. 6, pp. 393-400.

Ampofo et al., "Disaccharide compositional analysis of heparin and heparan sulfate using capillary zone electrophoresis", Analytical Biochemistry, 1991, vol. 199, pp. 249-255.

Ansel et al., "Pharmaceutical dosage forms and drug delivery systems", 1999, pp. 23-27 and 54-59, published by Lippincott Williams & Wilkins.

Anumula et al., "High resolution and high sensitivity methods for oligosaccharide mapping and characterization by normal phase high performance liquid chromatography following derivatization with highly fluorescent anthranilic acid", Glycobiology, 1998, vol. 8, No. 7, pp. 685-694.

Araki et al., "Application of 2-aminopyridine fluorescence labeling in the analysis of in vivo and in vitro metabolism of dextran sulfate sodium by size-exclusion high-performance liquid chromatorgraphy", J. Chromatography B Biomed. Sci., 2001, vol. 753, No. 2, pp. 209-215.

Bartolucci et al., "Inhibition of human leukocyte elastase by chemically and naturally oversulfated galactosaminoglycans", Carbohydrate Research, 1995, vol. 276, No. 2, pp. 401-408.

Bennett et al., "High resolution analysis of functional determinants on human tissue-type plasminogen activator", J. of Biological Chemistry, 1991, vol. 266, No. 8, pp. 5191-5201.

Bianchini et al., "Few bicyclic acetals at reducing end of low-molecular-weight heparins: might they restrict specification of pharmacopoeia?" Pharmeuropa Scientific Notes, 2005, vol. 1, pp. 1-3.

Bianchini et al., "Variability of heparins and heterogeneity of low molecular weight heparins" Seminars in Thrombosis and Hemostasis, 2007, vol. 33, No. 5, pp. 496-502.

Bigge et al., "Nonselective and efficient fluorescent labeling of glycans using 2-amino benzamide and anthranilic acid", Anal. Biochem., 1995, vol. 230, No. 2, pp. 229-238.

Binari et al., "Genetic evidence that heparin-like glycosaminoglycans are involved in wingless signaling", Development, 1997, vol. 124, pp. 2623-2632.

Bosch et al., "Recognition of BCR-ABL positive leukemic blasts by human CD4+ T cells elicited by primary in vitro immunization with a BCR-ABL breakpoint peptide", Blood, 1996, vol. 88, pp. 3522-3527.

Bottio et al., "Life threatening anaphylactic shock caused by porcine heparin intravenous infusion during mitral valve repair," The Journal of Thoracic and Cardiovascular Surgery, 2003, vol. 126, pp. 1194-1195.

Boël et al. "BAGE: a new gene encoding an antigen recognized on human melanomas by cytolytic T lymphocytes", Immunity, 1995, vol. 2, pp. 167-175.

Brichard et al., "A tyrosinase nonapeptide presented by HLA-B44 is recognized on a human melanoma by autologous cytolytic T lymphocytes", Eur. J. Immunol., 1996, vol. 26, pp. 224-230.

Brossart et al., "Her-2/neu-derived peptides are tumor-associated antigens expressed by human renal cell and colon carcinoma lines and are recognized by in vitro induced specific cytotoxic T lymphocytes", Cancer Res., 1998, vol. 58, pp. 732-736.

Brändle et al., "A mutated HLA-A2 molecule recognized by autologous cytotoxic T lymphocytes on a human renal cell carcinoma", J. Exp. Med., 1996, vol. 183, pp. 2501-2508.

Campbell, S. A., Filed by Amphastar pharmaceuticals in response to citizen petition docket No. 03P-0064/CP1 filed with the United States Food and Drug Administration. Response filed on May 13, 2004, Entered into FDA docket system on Jun. 8, 2004.

Carlson et al., "The Determination of recombinant human tissue-type plasminogen activator activity by turbidimetry using a microcentrifugal analyzer", Analytical Biochem., 1988, vol. 168, pp. 428-435.

Castelli et al., "Mass spectromic identification of a naturally processed melanoma peptide recognized by CD8+ cytotoxic T lymphocytes", J. Exp. Med., 1995, vol. 181, pp. 363-368.

Castelli et al., "Novel HLA-Cw8-restricted T cell epitopes derived from tyrosinase-related protein-2 and gp100 melanoma antigens", J. Immunol., 1999, vol. 162, pp. 1739-1748.

Cerny et al., "Preparation of 2-amino-1,6-anhydro-2,3-dideoxy-b-D-arabino-hexopyranose. 1H- and 13C-N.M.R. spectra of deoxy derivatives of 2-amino-1,6-deoxy-D-glucose and 2-amino-1,6-anhydro-2-deoxy-D-mannose", Carbohydrate Research, 1984, vol. 130, pp. 103-114.

Chaux et al. "Identification of five MAGE-A1 epitopes recognized by cytolytic T lymphocytes obtained by in vitro stimulation with dendritic cells transduced with MAGE-A1", J. Immunol., 1999, vol. 163, pp. 2928-2936.

Chaux et al., "Identification of MAGE-3 epitopes presented by HLA-DR molecules to CD4(+) T lymphocytes", J. Exp. Med., 1999, vol. 189, pp. 767-778.

Chiari et al., "Two antigens recognized by autologous cytolytic T lymphocytes on a melanoma result form a single point mutation in an essential housekeeping gene", Cancer Res., 1999, vol. 59, pp. 5785-5792.

Citizens Petition filed with the United Staes Food and Drug Administration by Aventis Pharmaceuticals Inc. on Feb. 19, 2003.

Citizens Petition Supplemental filed with the United Staes Food and Drug Administration by Aventis Pharmaceuticals Inc. on Feb. 12, 2004.

Collard et al., "A novel approach to 14C lable N-linked oligosaccharides" Analyt. Biochem., 1997, vol. 247, No. 2, pp. 448-450.

Correale et al., "In vitro generation of human cytotoxic T lymphocytes specific for peptides derived from prostate-specific antigen", J. Natl. Cancer Inst., 1997, vol. 89, pp. 293-300.

Coulie et al., "A mutated intron sequence codes for an antigenic peptide recognized by cytolytic T lymphocytes on a human melanoma", Proc. Natl. Acad. Sci., 1995, vol. 92, pp. 7976-7980.

Coulie, "Antigens recognized on human tumors by cytolytic lymphocytes: towards vaccination?", Stem Cells, 1995, vol. 13, pp. 393-403.

Cox et al., "Identification of a peptide recognized by five melanoma-specific human cytotoxic T cell lines", Science, 1994, vol. 264, pp. 716-719.

DA Col et at., "Characterization of the chemical structure of sulphated glycosaminoglycans after enzymatic digestion; Application for liquid chromatography-mass spectrometry with an atmospheric pressure interface", J. of Chromatography, 1993, vol. 647, pp. 289-300.

Dalmora et al., "Biological potency and physicochemical characterization of unfractionated heparins," Revista Brasileira de Hematologi e Hematerapia, 2009, vol. 31, No. 4, pp. 1-7.

Dawes et al., "The measurement of heparin and other therapeutic sulphated polysaccharides in plasma, serum and urine", Thrombosis and Haemostasis, 1985, vol. 54, No. 3, pp. 630-634.

De Backer et al., "Characterization of the GAGE genes that are expressed in various human cancers and in normal testis", Cancer Res., 1999, vol. 59, pp. 3157-3165.

Desai et al., "Oligosaccharide composition of heparin and low-molecular-weight heparin by capillary electrophoresis", Analytical Biochem., 1993, vol. 213, pp. 120-127.

Desai et al., "Molecular weight of low molecular weight heparins by 13C nuclear magnetic resonance spectroscopy", Carbohydrate Research, 1994, vol. 255, pp. 193-212.

Drummond et al., "Electrophoretic sequencing of heparin/heparan sulfate oligosaccharides using a highly sensitive fluorescent end label", Proteomics, 2001, vol. 1, No. 2, pp. 304-310.

Duffour et al., "A MAGE-A4 peptide presented by HLA-A2 is recognized by cytolytic T lymphocytes", Eur. J. Immunol., 1999, vol. 29, pp. 3329-3337.

Ernst et al., "Direct evidence for a predominantly exolytic processive mechanism for depolymerization of heparin-like glycosaminoglycans by heparinase I", PNAS USA, 1998, vol. 95, pp. 4182-4187.

Ernst et al., "Expression in *Escherichia coli*, purification and characterization of heparinase I from Flavobacterium heparinum", Biochem. J., 1996, vol. 315, pp. 589-597.

European Search Report from European Application Serial No. 10190250.0 dated Dec. 27, 2010.

Fareed et al., "Generic low-molecular-weight heparins: some practical considerations" Seminars in Thrombosis and Hemostasis, 2004, vol. 30, No. 6, pp. 703-713.

Fareed et al., "Biochemical and pharmacologic heterogeneity in low molecular weight heparins. Impact on the therapeutic profile", Current Pharmaceutical Design, 2004, vol. 10, pp. 983-999.

Fisk et al., "Identification of immunodominant peptide of HER-2/neu protooncogene recognized by ovarian tumor-specific cytotoxic T lymphocyte lines", J. Exp. Med., 1995, vol. 181, pp. 2109-2117.

Franz et al., "MALDI-FTMS characterization of oligosaccharides labeled with 9-aminofluorene", J. Am. Soc. Mass Spectrom., 2001, vol. 12, No. 12, pp. 1254-1261.

Fujie et al., "A MAGE-1-encoded HLA-A24-binding synthetic peptide induces specific anti-tumor cytotoxic T lymphocytes", Int. J. Cancer, 1999, vol. 80, pp. 169-172.

Gaudin et al., "A hsp70-2 mutation recognized by CTL on a human renal cell carcinoma", J. Immunol., 1999, vol. 162, pp. 1730-1738.

Gaugler et al., "Human gene MAGE-3 codes for an antigen recognized on a melanoma by autologous cytolytic T lymphocytes", J. Exp. Med., 1994, vol. 179, pp. 921-930.

Gjertsen et al., "Cytotoxic CD4+ and CD8+ T lymphocytes, generated by mutant p21-ras (12Val) peptide vaccination of a patient, recognize 12Val-dependent nested epitopes present within the vaccine peptide and kill autologous tumour cells carrying this mutation", Int. J. Cancer, 1997, vol. 72, pp. 784-790.

Guerrini et al., "Combined quantitative 1H and 13C nuclear magnetic resonance spectroscopy for characterization of heparin preparations", Seminars in Thrombosis and Hemostasis, 2001, vol. 27, No. 5, pp. 473-482.

Guerrini et al., "Complex glycosaminoglycans: profiling substitution patterns by two-dimensional nuclear magnetic resonance spectroscopy", Analytical Biochemistry, 2005, vol. 337, pp. 35-47.

Guerrini et al., "Low molecular weight heparins: structural differentiation by bidimensional nuclear magnetic resonance spectroscopy", Seminars in Thrombosis and Hemostasis, 2007, vol. 33, No. 5, pp. 478-487.

Guerrini et al., "Oversulfated chondroitin sulfate is a contaminant in heparin associated with adverse clinical events", Nature Biotechnology, Jun. 2008, vol. 26, No. 6, pp. 669-675, Nature Publishing Group US.

Guilloux et al., "A peptide recognized by human cytolytic T lymphocytes on HLA-A2 melanomas is encoded by an intron sequence of the N-acetylglucosaminyltransferase V gene", J. Exp. Med., 1996, vol. 183, pp. 1173-1183.

Guizzardi et al., "Pharmacokinetics and organ distribution in rats of a low molecular weight heparin", Arzneimittel-Forschung, 1987, vol. 37, No. 11, pp. 1281-1283.

Guo et al., "The disaccharide composition of heparins and heparan sulfates", Analytical Biochem., 1989, vol. 176, pp. 96-104.

Guéguen et al., "An antigen recognized by autologous CTLs on a human bladder carcinoma", J. Immunol., 1998, vol. 160, pp. 6188-6194.

Harenberg et al., "Overview on guidelines and recommendations for generic low-molecular-weight heparins", Thrombosis Research, vol. 127, S100-S104 (2011).

Hennekens et al., "Current issues concerning thrombolytic therapy of acute myocardial infarction", J. Am. Coll. Cardiol., 1995, vol. 25, No. 7, pp. 18S-22S.

Herman et al., "A peptide encoded by the human MAGE3 gene and presented by HLA-B44 induces cytolytic T lymphocytes that recognize tumor cells expressing MAGE3", Immunogenetics, 1996, vol. 43, pp. 377-383.

Hirano, "NMR study of 4-deoxy-a-L-threo-4-enohexopyranosyluronic acid (1® 3)2-acetamido-2-deoxy-D-hexoses produced in the enzymic digestion of hyaluronate, chondroitin and chondroitin sulfates", Organic Magnetic Resonance, vol. 2, pp. 577-580, 1970.

Hogan et al., "The peptide recognized by HLA-A68.2-restricted, squamous cell carcinoma of the lung-specific cytotoxic T lymphocytes is derived from a mutated elongation factor 2 gene", Cancer Res., 1998, vol. 58, pp. 5144-5150.

Holmes et al., "Lessons we have learned from the GUSTO trial", J. Am. Coll. Cardiol., 1995, vol. 25, No. 7, pp. 10S-17S.

Holzgrabe et al., "Quantitative NMR spectroscopy—Applications in drug analysis", Journal of Pharmaceutical and Biomedical Analysis, vol. 38, pp. 806-812, 2005.

Hricovini et al., "Conformational analysis of heparin epoxide in aqueous solution. An NMR relaxation study", Carbohydrate Research, 1995, vol. 277, pp. 11-23.

Huang et al., "Cytolytic T lymphocytes recognize an antigen encoded by MAGE-A10 on a human melanoma", J. Immunol., 1999, vol. 162, pp. 6849-6854.

Ikeda et al., "Characterization of an antigen that is recognized on a melanoma showing partial HLA loss by CTL expressing an NK inhibitory receptor", Immunity, 1997, vol. 6, pp. 199-208.

Imai et al., "Directional degradation of b-chitin by chitinase A1 revealed by a novel reducing end labelling technique", FEBS Lett, 2002, vol. 510, No. 3, pp. 201-205.

Imanari et al., "High-performance liquid chromatographic analysis of glycosaminglycan-derived oligosaccharides", J. of Chomatography A, 1996, vol. 720, pp. 275-293.

International Search Report and Written Opinion from International Application Serial No. PCT/US2009/055792 mailed Feb. 12, 2009.

International Search Report from International Application Serial No. PCT/US03/07208 dated Nov. 16, 2004.

Jeske et al., "Pharmacologic profile of certoparin", Exp. Opin. Invest. Drugs, 1999, vol. 8, No. 3, pp. 315-327.

Jäger et al., "Simultaneous humoral and cellular immune response against cancer-testis antigen NY-ESO-1: definition of human histocompatibility leukocyte antigen (HLA)-A2-binding peptide epitopes", J. Exp. Med., 1998, vol. 187, pp. 265-270.

Kang et al., "Identification of a tyrosinase epitope recognized by HLA-A24-restricted, tumor-infiltrating lymphocytes", J. Immunol., 1995, vol. 155, pp. 1343-1348.

Karamanos et al., "Ion-pair high-performance liquid chromatography for determining disaccharide composition in heparin and heparan sulphate", J. of Chromatography, 1997, vol. 765, pp. 169-179.

Kariya et al., "Disaccharide analysis of heparin and heparan sulfate using deaminative cleavage with nitrous acid and subsequent labeling with paranitrophenyl hydrazine", J. Biochem., 1998, vol. 123, No. 2, pp. 240-246, Tokyo.

Kawakami et al., "Identification of a human melanoma antigen recognized by tumor-infiltrating lymphocytes associated with in vivo tumor rejection", Proc. Natl. Acad. Sci. USA, 1994, vol. 91, pp. 6458-6462.

Kawakami et al., "Identification of new melanoma epitopes on melanosomal proteins recognized by tumor infiltrating T lymphocytes restricted by HLA-A1, -A2, and -A3 alleles", J. Immunol., 1998, vol. 161, pp. 6985-6992.

Kawakami et al., "Identification of the immunodominant peptides of the MART-1 human melanoma antigen recognized by the majority of HLA-A2-restricted tumor infiltrating lymphocytes", J. Exp. Med., 1994, vol. 180, pp. 347-352.

Kawakami et al., "Recognition of multiple epitopes in the human melanoma antigen gp100 by tumor-infiltrating T lymphocytes associated with in vivo tumor regression", J. Immunol., 1995, vol. 154, pp. 3961-3968.

Kawashima et al., "The multi-epitope approach for immunotherapy for cancer: identification of several CTL epitopes from various tumor-associated antigens expressed on solid epithelial tumors", Hum. Immunol., 1998, vol. 59, pp. 1-14.

Keiser et al., "Preimplantation screening for transgenesis using an embryonic specific promoter and green fluorescent protein", Cloning, 2001, vol. 3, No. 1, pp. 21-30.

Kinoshita et al., "Microanalysis of glycosaminoglycan-derived oligosaccharides labeled with a fluorophore 2-aminobenzamide by high-performance liquid chromatography: application to disaccharide composition analysis and exosequencing of oligosaccharides", Analytical Biochem., 1999, vol. 269, pp. 367-378.

Kishimoto et al., "Contaminated heparin associated with adverse clinical events and activation of the contact system", The New England Journal of Medicine, Apr. 23, 2008, vol. 358, No. 23, pp. 2457-2467.

Kishimoto et al., "MII8—A rationally engineered low-molecular-weight heparin designed specifically for the treatment of acute coronary syndromes", Thrombosis and Haemostasis, 1999, vol. 102. No. 5. pp. 900-906.

Kittlesen et al., "Human melanoma patients recognize an HLA-A1-restricted CTL epitope from tyrosinase containing two cysteine residues: implications for tumor vaccine development", J. Immunol., 1998, vol. 160, pp. 2099-2106.

Kobayashi et al., "CD4+ T cells from peripheral blood of a melanoma patient recognize peptides derived from nonmutated tyrosinase", Cancer Research, 1998, vol. 58, pp. 296-301.

Kuhle et al., "Pharmacokinetic study of tinzaparin in pediatric patients", Blood, 2002, vol. 100, No. 11, Abstract No. 3975.

Lamari et al., "Analysis of glycosaminoglycan-derived disaccharides in biologic samples by capillary electrophoresis and protocol for sequencing glycosaminoglycans", Biomedical Chromatography, 2002, vol. 16, pp. 95-102.

Langer "New methods of drug delivery", Science, 1990, vol. 249, pp. 1527-1533.

Larnkjaer et al., "Binding of Low Molecular Weight Heprin (Tinzaparin sodium) to Bovine Endothelial Cells in vitro" Thrombosis Res., vol. 75., No. 2, pp. 185-194 (1994).

Lee et al., "Separation of reduced disaccharides derived from glycosaminoglycans by high-performance liquid chromatography", J. of Chromatography, 1981, vol. 212, pp. 65-73.

Li et al., "Linkage analysis of chromophore-labeled disaccharides and linear oligosaccharides by negative ion fast atom bombardment ionization and collisonal-induced dissociation with B/E scanning", Analyt. Biochem., 1993, vol. 211, No. 2, pp. 250-257.

Lin et al., "Heparan sulfate proteoglycans are essential for FGF receptor signaling during *Drosophila* embryonic development", Development, 1999, vol. 126, pp. 3715-3723.

Lindahl et al., "Common binding sites for b-amyloid fibrils and fibroblast growth factor-2 in heparan sulfate from human cerebral cortex", J. Biol. Chem., 1999, vol. 274, pp. 30631-30635.

Lindhart et al., "Mapping and quantification of the major oligosaccharide components of heparin", Biochem. Journal, 1988, vol. 254, pp. 781-787.

\* cited by examiner 2.10 ppm ppm (t1)

EVALUATING HEPARIN PREPARATIONS

This application claims priority to U.S. application Ser. No. 61/296,218, filed on Jan. 19, 2010, and U.S. Application Ser. No. 61/374,950, filed on May 25, 2010. The disclosure of the prior applications are considered part of (and are incorporated by reference in) the disclosure of this application.

BACKGROUND

Complex polysaccharides have been used as pharmaceutical interventions in a number of disease processes, including oncology, inflammatory diseases, and thrombosis. Examples of pharmaceutical interventions in this class are hyaluronic acid, an aid to wound healing and anti-cancer agent, and heparin, a potent anticoagulant and anti-thrombotic agent. Complex polysaccharides elicit their function primarily through binding soluble protein signaling molecules, including growth factors, cytokines and morphogens present at the cell surface and within the extracellular matrices between cells, as well as their cognate receptors present within this environment. In so doing, these complex polysaccharides effect critical changes in extracellular and intracellular signaling pathways important to cell and tissue function. For example, heparin binds to the coagulation inhibitor anti-thrombin III promoting its ability to inhibit factor IIa and Xa.

SUMMARY

In one aspect, the disclosure features a method of identifying if a process was used to make a heparin preparation (e.g., an unfractionated heparin preparation or a low molecular weight heparin (LMWH) preparation). The method includes:

determining if a structural signature associated with a peak in the N-acetyl region of a $^1$H 1D-NMR spectra, e.g., a structural signature associated with the peak at 2.08 ppm of FIG. 9 and/or the peak at 2.10 ppm of FIG. 1, is absent from or present in a heparin preparation wherein the presence of the structural signature indicates that the heparin preparation was made by a method (e.g., a method that includes oxidation or oxidation followed by treatment with an acid) and the absence of the structural signature indicates that the heparin preparation was not made by the method (e.g., the method did not include oxidation or oxidation followed by treatment with an acid); and making a decision or step regarding the heparin preparation if the heparin preparation was made by the method (e.g., the method includes oxidation or oxidation followed by treatment with an acid) or if the heparin preparation was not made by the method (e.g., the method does not include oxidation or oxidation followed by treatment with an acid), e.g., the heparin preparation is classified, selected, accepted or discarded, released or withheld, processed into a drug product, shipped, moved to a new location, formulated, labeled, packaged, released into commerce, sold, or offered for sale.

In one embodiment, the method includes making a decision or step regarding the heparin preparation if the heparin preparation was made by the method (e.g., the method includes oxidation or oxidation followed by treatment with an acid), e.g., the decision or step is to classify, select, accept, release, process into a drug product, ship, formulate, label, package, release into commerce, sell, or offer for sale.

In another embodiment, the method includes making a decision or step regarding the heparin preparation if the heparin preparation was not made by the method (e.g., the method did not include oxidation or oxidation followed by treatment with an acid), e.g., the decision or step is to discard or withhold the heparin sample.

In one embodiment, the method can be used to determine suitability of the heparin preparation for use as a pharmaceutical or for use in making a pharmaceutical. In an embodiment, the heparin preparation is selected from the group of a starting material for the production of a drug, an intermediate in the production of a drug, a drug substance or a drug product.

In one embodiment, the heparin preparation is an unfractionated heparin preparation and the decision or step includes selecting the unfractionated heparin preparation for further processing, e.g., to produce a LMWH preparation, e.g., a LMWH preparation described herein. In one embodiment, the heparin preparation is selected for depolymerization, e.g., chemical and/or enzymatic depolymerization, and/or size fractionation to produce a LMWH preparation, e.g., a LMWH preparation described herein.

In one embodiment, the method further includes selecting the heparin preparation and processing the heparin preparation, e.g., to produce a drug product. In one embodiment, the heparin preparation is an unfractionated heparin preparation and the method further comprises depolymerizing the unfractionated heparin preparation, e.g., by chemical and/or enzymatic depolymerization, to produce a LMWH preparation, e.g., a LMWH preparation described herein. In one embodiment, the heparin preparation is an unfractionated heparin preparation and the method further comprises size fractionation of the unfractionated heparin preparation to produce a LMWH preparation, e.g., a LMWH preparation described herein. In one embodiment, the heparin preparation is an unfractionated heparin preparation and the method further comprises depolymerization and size fractionation of the unfractionated heparin preparation to produce a LMWH preparation, e.g., a LMWH preparation described herein. In one embodiment, the heparin preparation is an unfractionated heparin preparation and the method further comprises processing the unfractionated heparin preparation by one or more of the methods described herein.

In one embodiment, the heparin preparation is a commercially available unfractionated heparin preparation, e.g., a commercially available unfractionated heparin preparation described herein.

In one embodiment, the heparin preparation is a LMWH preparation and the decision or step is selecting, accepting, releasing, processing into a drug product, shipping, formulating, labeling, packaging, releasing into commerce, selling, or offering for sale the LMWH preparation.

In one embodiment, the LMWH preparation is a LMWH preparation described herein.

In an embodiment, the method further includes memorializing the decision or step taken.

In one embodiment, if the structural signature is present, the method further comprises determining the amount of the structural signature present in the heparin preparation.

In one embodiment, the absence or presence of the structural signature associated with the peak at 2.08 ppm of FIG. 9 and the structural signature associated with the peak at 2.10 ppm of FIG. 1 are determined.

In one embodiment, the presence of the structural signature associated with the peak at 2.10 ppm of FIG. 1 indicates that the heparin preparation was made by a method that includes oxidation. In one embodiment, the presence of the structural signature associated with the peak at 2.08 ppm of FIG. 9 indicates that the heparin preparation was made by a method that includes oxidation and treatment with an acid.

In one embodiment, the structural signature is associated with a modification on or near an N-acetylglucosamine. In one embodiment, the structural signature is associated with a modification on or near an N-acetylglucosamine residue at the reducing end of chains within a heparin preparation.

In one embodiment, the structural signature is one or more of:

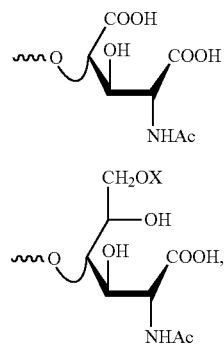

wherein in structure B, X=H or $SO_3$

In one embodiment, the absence or presence of the structural signature is determined using one or more of using high performance liquid chromatography (HPLC), nuclear magnetic resonance (NMR) (e.g., 1D-NMR or 2D-NMR), capillary electrophoresis (CE), mass spectroscopy (e.g., matrix-assisted laser desorption ionization-mass spectroscopy (MALDI-MS), electrospray ionization-mass spectroscopy (ESI-MS)), and fast protein liquid chromatography (FPLC).

In another aspect, the disclosure features a method of identifying if a process was used to make a heparin preparation (e.g., an unfractionated heparin preparation or low molecular weight heparin (LMWH) preparation), comprising:

acquiring a value, e.g., obtained by a separation method, which indicates the absence, presence or amount of a structural signature associated with a peak in the N-acetyl region of a $^1$H 1D-NMR spectra, e.g., a structural signature associated with the peak at 2.08 ppm of FIG. 9 and/or the peak at 2.10 ppm of FIG. 1, in a heparin preparation;

determining if the heparin preparation was made by a method (e.g., a method that includes oxidation of the heparin preparation or oxidation followed by treatment with an acid), wherein the presence of the structural signature indicates that the heparin preparation was made by the method (e.g., the method includes oxidation or oxidation followed by treatment with an acid) and the absence of the structural signature indicates that that the heparin preparation was not made by the method (e.g., the method did not include oxidation or oxidation followed by treatment with an acid); and making a decision or step regarding the heparin preparation if the heparin preparation was made by the method (e.g., the method includes oxidation or oxidation followed by treatment with an acid) or if the heparin preparation was not made by the method (e.g., the method does not include oxidation or oxidation followed by treatment with an acid), e.g., the heparin preparation is classified, selected, accepted or discarded, released or withheld, processed into a drug product, shipped, moved to a new location, formulated, labeled, packaged, released into commerce, sold, or offered for sale.

In one embodiment, the method includes making a decision or step regarding the heparin preparation if the heparin preparation was made by the method (e.g., the method includes oxidation or oxidation followed by treatment with an acid), e.g., the decision or step is to classify, select, accept, release, process into a drug product, ship, formulate, label, package, release into commerce, sell, or offer for sale.

In another embodiment, the method includes making a decision or step regarding the heparin preparation if the heparin preparation was not made by the method (e.g., the method did not include oxidation or oxidation followed by treatment with an acid), e.g., decision or step is to discard or withhold the heparin preparation.

In one embodiment, the method can be used to determine suitability of the heparin preparation for use as a pharmaceutical or for use in making a pharmaceutical. In an embodiment, the heparin preparation is selected from the group of a starting material for the production of a drug, an intermediate in the production of a drug, a drug substance or a drug product.

In one embodiment, the heparin preparation is an unfractionated heparin preparation and the decision or step includes selecting the unfractionated heparin preparation for further processing, e.g., to produce a LMWH preparation, e.g., a LMWH preparation described herein. In one embodiment, the heparin preparation is selected for depolymerization, e.g., chemical and/or enzymatic depolymerization, and/or size fractionation to produce a LMWH preparation, e.g., a LMWH preparation described herein.

In one embodiment, the method further includes selecting the heparin preparation and processing the heparin preparation, e.g., to produce a drug product, e.g., by one or more of the methods described herein.

In one embodiment, the heparin preparation is a commercially available unfractionated heparin preparation, e.g., a commercially available unfractionated heparin preparation described herein.

In one embodiment, the heparin preparation is a LMWH preparation and the decision or step is selecting, accepting, releasing, processing into a drug product, shipping, formulating, labeling, packaging, releasing into commerce, selling, or offering for sale the LMWH preparation.

In one embodiment, the LMWH preparation is a LMWH preparation described herein.

In an embodiment, the method further includes memorializing the decision or step taken.

In one embodiment, if the structural signature is present, the evaluation includes the amount of the structural signature present in the heparin preparation.

In one embodiment, the evaluation indicates the absence or presence of the structural signature associated with the peak at 2.08 ppm of FIG. 9 and the structural signature associated with the peak at 2.10 ppm of FIG. 1.

In one embodiment, the presence of the structural signature associated with the peak at 2.10 ppm of FIG. 1 indicates that the heparin preparation was made by a method that includes oxidation. In one embodiment, the presence of the structural signature associated with the peak at 2.08 ppm of FIG. 9 indicates that the heparin preparation was made by a method that includes oxidation and treatment with an acid.

In one embodiment, the structural signature is associated with a modification on or near an N-acetylglucosamine. In one embodiment, the structural signature is associated with a modification on or near an N-acetylglucosamine residue at the reducing end of chains within a heparin preparation.

In one embodiment, the structural signature is one or more of:

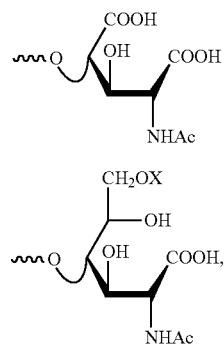

wherein in structure B, X=H or SO$_3$.

In one embodiment, the separation method is one or more separation method described herein.

In another aspect, the disclosure features a method of identifying if a process was used to make a heparin preparation (e.g., an unfractionated heparin preparation or low molecular weight heparin (LMWH) preparation), comprising:

using a separation method to determine the absence or presence of a structural signature associated a peak in the N-acetyl region of a $^1$H 1D-NMR spectra, e.g., a structural signature associated with the peak at 2.08 ppm of FIG. 9 and/or the peak at 2.10 ppm of FIG. 1, in a heparin preparation; and determining if the heparin preparation was made by a method (e.g., a method that includes oxidation of the heparin preparation or oxidation followed by treatment with an acid), wherein the presence of the structural signature indicates that the heparin preparation was made by the method (e.g., the method includes oxidation of the heparin preparation or oxidation followed by treatment with an acid) and the absence of the structural signature indicates that the heparin preparation was not made by the method (e.g., the method did not include oxidation of the heparin preparation or oxidation followed by treatment of the heparin preparation with an acid).

In an embodiment, the method further includes making a decision or step regarding the heparin preparation if the heparin preparation was made by the method (e.g., the method includes oxidation or oxidation followed by treatment with an acid) or if the heparin preparation was not made by the method (e.g., the method does not include oxidation or oxidation followed by treatment with an acid), e.g., the heparin preparation is classified, selected, accepted or discarded, released or withheld, processed into a drug product, shipped, moved to a new location, formulated, labeled, packaged, released into commerce, sold, or offered for sale.

In one embodiment, the method can be used to determine suitability of the heparin preparation for use as a pharmaceutical or for use in making a pharmaceutical. In an embodiment, the heparin preparation is selected from the group of a starting material for the production of a drug, an intermediate in the production of a drug, a drug substance or a drug product.

In one embodiment, the heparin preparation is an unfractionated heparin preparation and the method further includes selecting the unfractionated heparin preparation for further processing, e.g., to produce a LMWH preparation, e.g., a LMWH preparation described herein. In one embodiment, the heparin preparation is selected for depolymerization, e.g., chemical and/or enzymatic depolymerization, and/or size fractionation to produce a LMWH preparation, e.g., a LMWH preparation described herein.

In one embodiment, the method further includes selecting the heparin preparation and processing the heparin preparation, e.g., to produce a drug product, e.g., by one or more of the methods described herein.

In one embodiment, the heparin preparation is a commercially available unfractionated heparin preparation, e.g., a commercially available unfractionated heparin preparation described herein.

In one embodiment, the heparin preparation is a LMWH preparation and the method further includes making a decision or a step. For example, the decision or step can be selecting, accepting, releasing, processing into a drug product, shipping, formulating, labeling, packaging, releasing into commerce, selling, or offering for sale the LMWH preparation. In an embodiment, the method further includes memorializing the decision or step taken.

In one embodiment, the LMWH preparation is a LMWH preparation described herein.

In one embodiment, if the structural signature is present, the method further comprises determining the amount of the structural signature present in the heparin preparation.

In one embodiment, the absence or presence of the structural signature associated with the peak at 2.08 ppm of FIG. 9 and the structural signature associated with the peak at 2.10 ppm of FIG. 1 are determined.

In one embodiment, the presence of the structural signature associated with the peak at 2.10 ppm of FIG. 1 indicates that the heparin preparation was made by a method that includes oxidation. In one embodiment, the presence of the structural signature associated with the peak at 2.08 ppm of FIG. 9 indicates that the heparin preparation was made by a method that includes oxidation and treatment with an acid.

In one embodiment, the structural signature is associated with a modification on or near an N-acetylglucosamine. In one embodiment, the structural signature is associated with a modification on or near an N-acetylglucosamine at the reducing end of chains within a heparin preparation.

In one embodiment, the structural signature is one or more of:

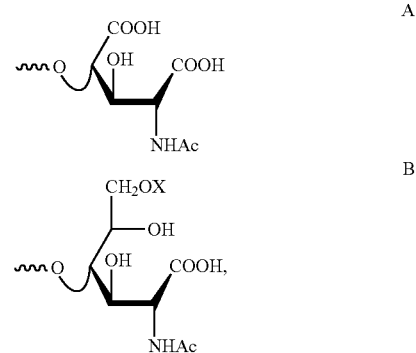

wherein in structure B, X=H or SO$_3$

In one embodiment, the absence or presence of the structural signature is determined using one or more separation method described herein.

In another aspect, the disclosure features a method of producing a heparin preparation (e.g., an unfractionated heparin preparation or low molecular weight heparin (LMWH) preparation), comprising:

using a separation method to determine the absence or presence of a structural signature associated a peak in the N-acetyl region of a $^1$H 1D-NMR spectra, e.g., a structural signature associated with the peak at 2.08 ppm of FIG. 9 and/or the peak at 2.10 ppm of FIG. 1, in a heparin preparation; and determining if the heparin preparation was made by a method (e.g., a method that includes oxidation of the heparin preparation or oxidation followed by treatment with an acid), wherein the presence of the structural signature indicates that the heparin preparation was made by the method (e.g., the method includes oxidation of the heparin preparation or oxidation followed by treatment with an acid) and the absence of the structural signature indicates that the heparin preparation was not made by the method (e.g., the method did not include oxidation of the heparin preparation or oxidation followed by treatment of the heparin preparation with an acid), and based upon the determination, making a decision or step regarding the heparin preparation if the heparin preparation was made by the method (e.g., the method includes oxidation or oxidation followed by treatment with an acid) or if the heparin preparation was not made by the method (e.g., the method does not include oxidation or oxidation followed by treatment with an acid), e.g., the heparin preparation is classified, selected, accepted or discarded, released or withheld, processed into a drug product, shipped, moved to a new location, formulated, labeled, packaged, released into commerce, sold, or offered for sale.

In one embodiment, the method can be used to determine suitability of the heparin preparation for use as a pharmaceutical or for use in making a pharmaceutical. In an embodiment, the heparin preparation is selected from the group of a starting material for the production of a drug, an intermediate in the production of a drug, a drug substance or a drug product.

In one embodiment, the heparin preparation is an unfractionated heparin preparation and the method further includes selecting the unfractionated heparin preparation for further processing, e.g., to produce a LMWH preparation, e.g., a LMWH preparation described herein. In one embodiment, the heparin preparation is selected for depolymerization, e.g., chemical and/or enzymatic depolymerization, and/or size fractionation to produce a LMWH preparation, e.g., a LMWH preparation described herein.

In one embodiment, the method further includes selecting the heparin preparation and processing the heparin preparation, e.g., to produce a drug product, e.g., by one or more of the methods described herein.

In one embodiment, the heparin preparation is a commercially available unfractionated heparin preparation, e.g., a commercially available unfractionated heparin preparation described herein.

In one embodiment, the heparin preparation is a LMWH preparation and the method further includes making a decision or a step. For example, the decision or step can be selecting, accepting, releasing, processing into a drug product, shipping, formulating, labeling, packaging, releasing into commerce, selling, or offering for sale the LMWH preparation. In an embodiment, the method further includes memorializing the decision or step taken.

In one embodiment, the LMWH preparation is a LMWH preparation described herein.

In one embodiment, if the structural signature is present, the method further comprises determining the amount of the structural signature present in the heparin preparation.

In one embodiment, the absence or presence of the structural signature associated with the peak at 2.08 ppm of FIG. 9 and the structural signature associated with the peak at 2.10 ppm of FIG. 1 are determined.

In one embodiment, the presence of the structural signature associated with the peak at 2.10 ppm of FIG. 1 indicates that the heparin preparation was made by a method that includes oxidation. In one embodiment, the presence of the structural signature associated with the peak at 2.08 ppm of FIG. 9 indicates that the heparin preparation was made by a method that includes oxidation and treatment with an acid.

In one embodiment, the structural signature is associated with a modification on or near an N-acetylglucosamine. In one embodiment, the structural signature is associated with a modification on or near an N-acetylglucosamine at the reducing end of chains within a heparin preparation.

In one embodiment, the structural signature is one or more of:

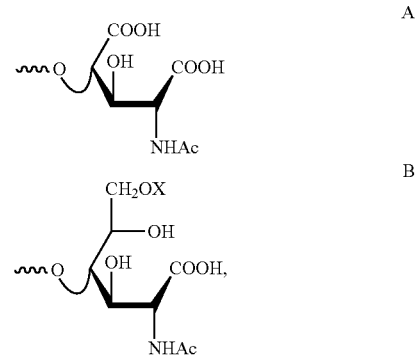

wherein in structure B, X=H or $SO_3$.

In one embodiment, the absence or presence of the structural signature is determined using one or more separation method described herein.

In another aspect, the disclosure features a method of determining if a heparin preparation (e.g., an unfractionated heparin preparation or a low molecular weight heparin (LMWH) preparation) is at risk for coloration, comprising:

determining if a structural signature associated with the peak at 2.10 ppm of the $^1$H 1D-NMR spectra of FIG. 1 is absent from or present in a heparin preparation wherein the presence of the structural signature indicates that the heparin preparation is not at risk for coloration and the absence of the structural signature indicates that that the heparin preparation is at risk for coloration; and making a decision or step regarding the heparin preparation if the heparin preparation is not at risk for coloration, e.g., the heparin preparation is classified, selected, accepted, released, processed into a drug product, shipped, moved to a new location, formulated, labeled, packaged, released into commerce, sold, or offered for sale, or if the heparin preparation is at risk for coloration, e.g., the heparin preparation is discarded or withheld.

In an embodiment, the heparin preparation is an unfractionated heparin preparation that is not at risk for coloration and the decision or step can be selecting he unfractionated heparin for further processing, e.g., by a method described herein. In one embodiment, the method further includes selecting a heparin preparation that is not at risk for coloration and processing the heparin preparation, e.g., by a method described herein.

In one embodiment, the heparin preparation is a commercially available unfractionated heparin preparation, e.g., a commercially available unfractionated heparin preparation described herein. In an embodiment, the heparin preparation is a LMWH preparation, e.g., a LMWH preparation described herein.

In one embodiment, the structural signature is associated with a modification on or near an N-acetylglucosamine. In one embodiment, the structural signature is associated with a modification on or near an N-acetylglucosamine residue at the reducing end of chains within a heparin preparation.

In one embodiment, the structural signature is one or more of:

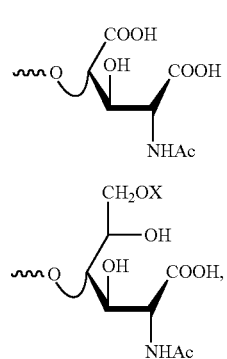

wherein in structure B, X=H or $SO_3$.

In an embodiment, the method further includes memorializing the decision or step taken.

In one embodiment, if the structural signature is present, the method further comprises determining the amount of the structural signature present in the heparin preparation.

In one embodiment, the absence or presence of the structural signature is determined using a separation method, e.g., a separation method described herein.

In another aspect, the disclosure features a method of determining if a heparin preparation (e.g., an unfractionated heparin preparation or a low molecular weight heparin (LMWH) preparation) is at risk for coloration, comprising:

acquiring a value, e.g., obtained by a separation method, indicating the absence, presence or amount of a structural signature associated with the peak at 2.10 ppm of the $^1$H 1D-NMR spectra of FIG. 1, in a heparin preparation;

determining if the heparin preparation is at risk for coloration or is not at risk for coloration, wherein the presence of the structural signature indicates that the heparin preparation is not at risk for coloration and the absence of the structural signature indicates that that the heparin preparation is at risk for coloration; and making a decision or step regarding the heparin preparation if the heparin preparation is not at risk for coloration, e.g., the heparin preparation is classified, selected, accepted, released, processed into a drug product, shipped, moved to a new location, formulated, labeled, packaged, released into commerce, sold, or offered for sale, or if the heparin preparation is at risk of coloration, e.g., the heparin preparation is discarded or withheld.

In an embodiment, the heparin preparation is an unfractionated heparin preparation that is not at risk for coloration and the decision or step can be selecting he unfractionated heparin for further processing, e.g., by a method described herein. In one embodiment, the method further includes selecting a heparin preparation that is not at risk for coloration and processing the heparin preparation, e.g., by a method described herein.

In one embodiment, the heparin preparation is a commercially available unfractionated heparin preparation, e.g., a commercially available unfractionated heparin preparation described herein. In an embodiment, the heparin preparation is a LMWH preparation, e.g., a LMWH preparation described herein.

In one embodiment, the structural signature is associated with a modification on or near an N-acetylglucosamine. In one embodiment, the structural signature is associated with a modification on or near an N-acetylglucosamine residue at the reducing end of chains within a heparin preparation.

In one embodiment, the structural signature is one or more of:

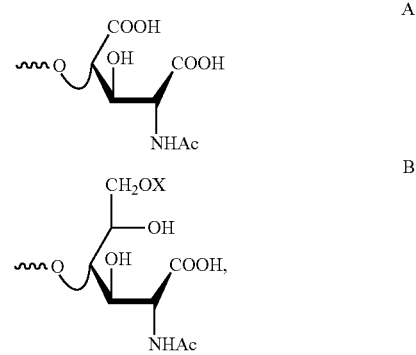

wherein in structure B, X=H or $SO_3$.

In an embodiment, the method further includes memorializing the decision or step taken.

In one embodiment, if the structural signature is present, the method further comprises determining the amount of the structural signature present in the heparin preparation.

In one embodiment, the absence or presence of the structural signature is determined using a separation method, e.g., a separation method described herein.

In another aspect, the disclosure features a method of determining if a heparin preparation (e.g., an unfractionated heparin preparation or a low molecular weight heparin (LMWH) preparation) is at risk for coloration, comprising:

using a separation method to determine the absence or presence of a structural signature associated with the peak at 2.10 ppm of the $^1$H 1D-NMR spectra of FIG. 1, in a heparin preparation; and determining if the heparin preparation is at risk for coloration or is not at risk for coloration, wherein the presence of the structural signature indicates that the heparin preparation is not at risk for coloration and the absence of the structural signature indicates that that the heparin preparation is at risk for coloration.

In an embodiment, the method further includes making a decision or step regarding the heparin preparation if the heparin preparation is not at risk for coloration, e.g., the heparin preparation is classified, selected, accepted, released, processed into a drug product, shipped, moved to a new location, formulated, labeled, packaged, released into commerce, sold, or offered for sale, or if the heparin preparation is at risk for coloration, e.g., the heparin preparation is discarded or withheld.

In an embodiment, the heparin preparation is an unfractionated heparin preparation that is not at risk for coloration and the decision or step can be selecting he unfractionated heparin for further processing, e.g., by a method described herein. In one embodiment, the method further includes selecting a heparin preparation that is not at risk for coloration and processing the heparin preparation, e.g., by a method described herein.

In one embodiment, the heparin preparation is a commercially available unfractionated heparin preparation, e.g., a commercially available unfractionated heparin preparation described herein. In an embodiment, the heparin preparation is a LMWH preparation, e.g., a LMWH preparation described herein.

In one embodiment, the structural signature is associated with a modification on or near an N-acetylglucosamine. In one embodiment, the structural signature is associated with a modification on or near an N-acetylglucosamine residue at the reducing end of chains within a heparin preparation.

In one embodiment, the structural signature is one or more of:

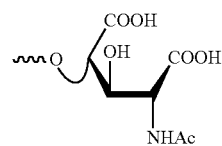

A

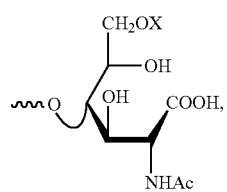

B wherein in structure B, X=H or SO$_3$.

In an embodiment, the method further includes memorializing the decision or step taken.

In one embodiment, if the structural signature is present, the method further comprises determining the amount of the structural signature present in the heparin preparation.

In one embodiment, the absence or presence of the structural signature is determined using a separation method, e.g., a separation method described herein.

In another aspect, the disclosure features a method of identifying a structural signature that is indicative of a method used to make a heparin preparation (e.g., an unfractionated heparin preparation or low molecular weight heparin (LMWH) preparation), comprising:

providing (e.g., acquiring) an evaluation of a structural signature or signatures associated with a peak in the N-acetyl region of a $^1$H 1D-NMR spectra of a first heparin preparation made by a first method;

providing (e.g., acquiring) an evaluation of a structural signature or signatures associated with a peak in the N-acetyl region of a $^1$H 1D-NMR spectra of a second heparin preparation made by a second method that differs from the first method;

identifying a structural signature associated with a peak in the N-acetyl region of a $^1$H 1D-NMR spectra of the first heparin preparation that is present in the first heparin preparation and is absent or present in a different amount in the second heparin preparation; and identifying the structural signature associated with a peak in the N-acetyl region of a $^1$H 1D-NMR spectra of the first heparin preparation or the amount of the structural signature associated with a peak in the N-acetyl region of a $^1$H 1D-NMR spectra of the first heparin preparation as a reference standard for identifying a heparin preparation made by the first method.

In one embodiment, the reference standard is memorialized, e.g., in print or in a computer readable record.

In one embodiment, the evaluation was obtained using a separation method, e.g., a separation method described herein.

In one embodiment, the heparin preparation is a commercially available unfractionated heparin preparation, e.g., a commercially available unfractionated heparin preparation described herein. In an embodiment, the heparin preparation is a LMWH preparation, e.g., a LMWH preparation described herein.

In one aspect, the disclosure features a method of analyzing a heparin preparation (e.g., an unfractionated heparin preparation or low molecular weight heparin (LMWH) preparation), comprising:

providing (e.g., acquiring) a value indicative of the absence, presence or amount of a structural signature or signatures associated with a peak in the N-acetyl region of a $^1$H 1D-NMR spectra of a heparin preparation, and comparing the value to a reference standard, e.g., a reference standard identified by a method described herein, to determine if the heparin preparation has a structural signature that identifies the method used to make the heparin sample, wherein the presence of the structural signature indicates that the heparin sample was made by a method and the absence of the structural signature indicates that that the heparin sample was not made by the method; and optionally, making a decision or step regarding the heparin sample if the heparin sample was made by the method, e.g., the heparin sample is classified, selected, accepted or discarded, released or withheld, processed into a drug product, shipped, moved to a new location, formulated, labeled, packaged, released into commerce, sold, or offered for sale.

In one embodiment, the decision or step is memorialized.

In one embodiment, the structural signature is determined using a separation method, e.g., a separation method described herein.

In one embodiment, the heparin preparation is a commercially available unfractionated heparin preparation, e.g., a commercially available unfractionated heparin preparation described herein. In an embodiment, the heparin preparation is a LMWH preparation, e.g., a LMWH preparation described herein.

In one aspect, the disclosure features a database that correlates the presence or amount of a structural signature associated with a peak in the N-acetyl region of a $^1$H 1D-NMR spectra, e.g., a peak at 2.08 ppm of FIG. 9 and/or the peak at 2.10 ppm of FIG. 1, with a method used to make the heparin preparation (e.g., a method that includes oxidation and/or treatment with an acid).

In one embodiment, the structural signature is associated with a modification on or near an N-acetylglucosamine. In one embodiment, the structural signature is associated with a modification on or near an N-acetylglucosamine residue at the reducing end of chains within a heparin preparation.

In one embodiment, the structural signature is one or more of:

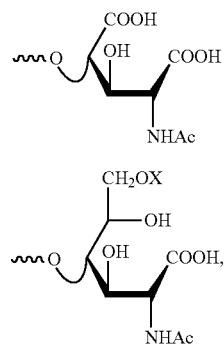

wherein in structure B, X=H or SO$_3$.

The details of one or more embodiments are set forth in the accompanying drawings and the description below. Other features, objects, and advantages of the invention will be apparent from the description and drawings, and from the claims.

DETAILED DESCRIPTION

The drawings are first briefly described.

FIG. 1 depicts $^1$H 1D-proton NMR spectra of an unfractionated heparin sodium (N-acetyl region). FIG. 1A depicts the spectra of an unfractionated heparin sodium sample with spiked an over sulfated chondrotin sulfate standard. FIG. 1B depicts the spectra of the unfractionated heparin sodium that was not spiked with the standard. The peak marked with an asterisk represents the peak at 2.10 ppm.

Figure 4A:
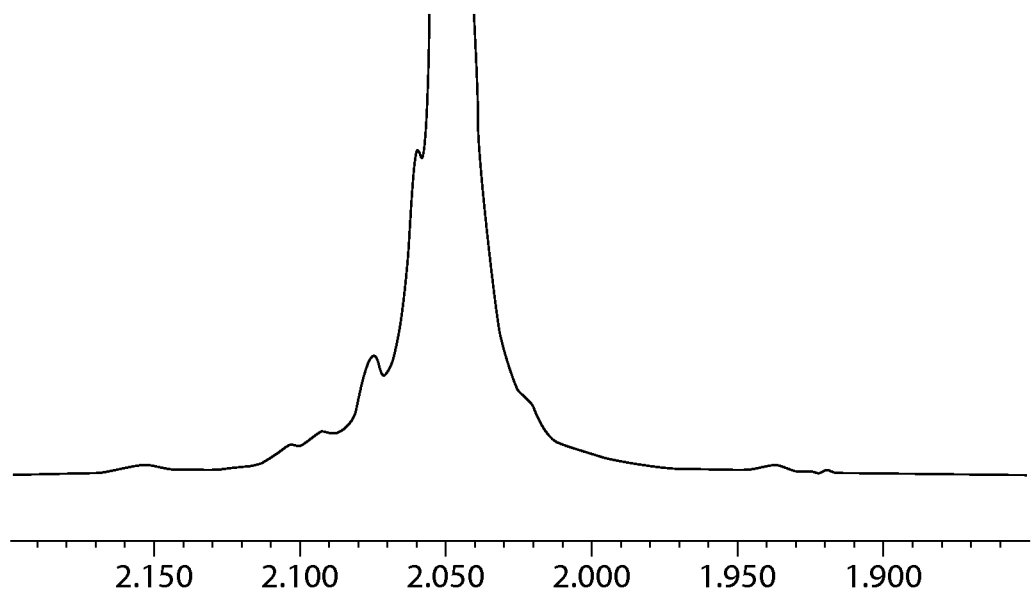
Figure 4B:
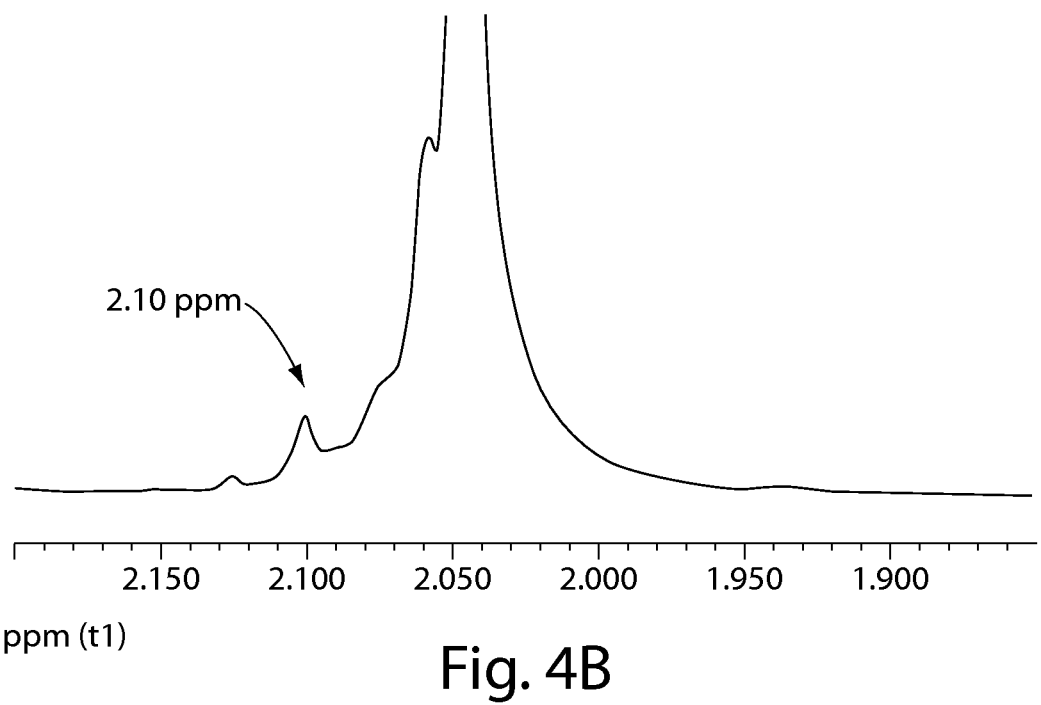

FIG. 4 depicts an expanded $^1$H 1D-NMR spectra of an unfractionated heparin sodium treated with different oxidation procedures. FIG. 4A depicts the spectra of an unfractionated heparin sodium treated with hydrogen peroxide; FIG. 4B depicts the spectra of an unfractionated heparin preparation treated with potassium permanganate.

Figure 5:
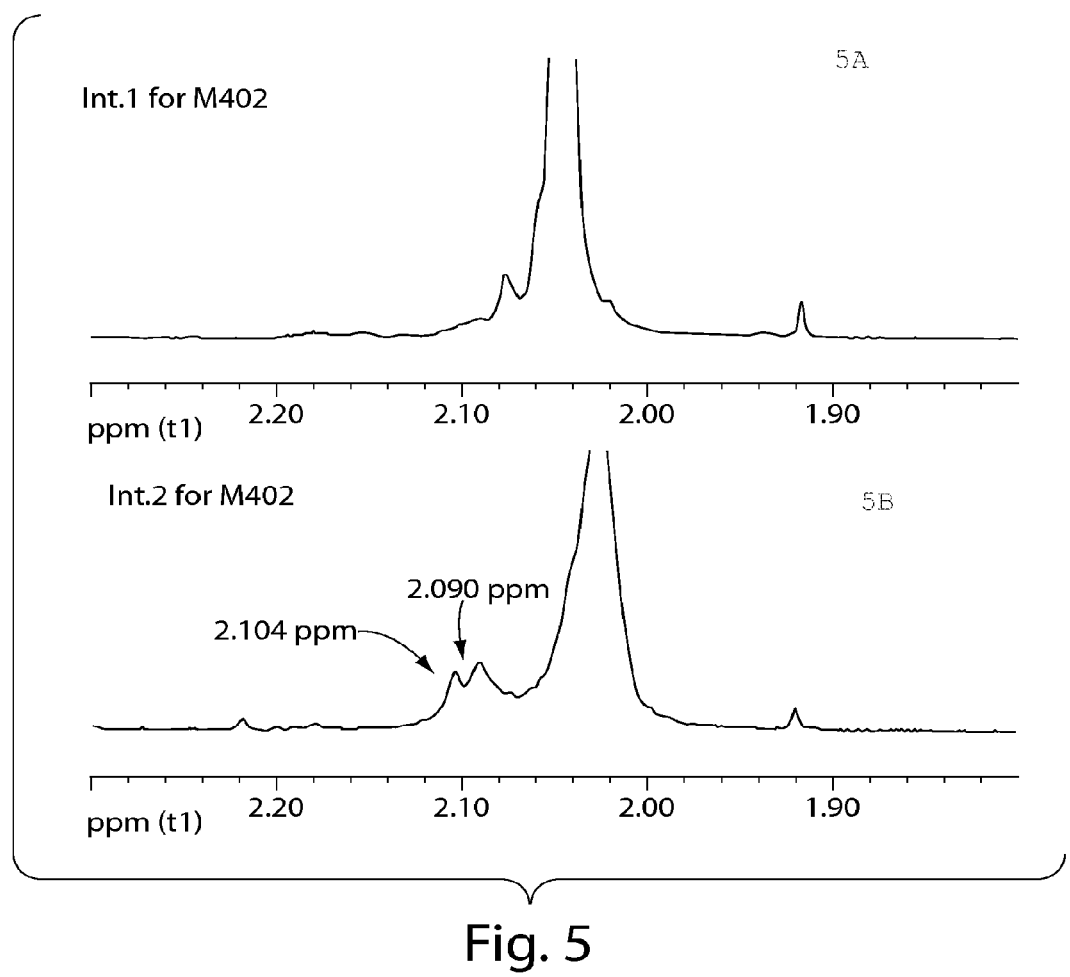

FIG. 5 depicts an expanded 1H 1D-NMR spectra of intermediates of a LMWH preparation before and after treatment with sodium periodate. FIG. 5A depicts the spectra of a starting LMWH, intermediate 1, which has not been subjected to an oxidative process. FIG. 5B depicts the spectra of intermediate 1, namely intermediate 2, after oxidation with sodium periodate.

FIG. 6 depicts an expanded $^1$H 1D-NMR spectra of a porcine intestine heparan sulfate preparation before and after treatment with potassium permanganate and a porcine intestinal heparin sulfate enriched in reducing end N-acetylglucosamine residues. FIG. 6A depicts the spectra of a porcine intestine heparan sulfate (HS) preparation. FIG. 6B depicts the spectra of the HS preparation after oxidation with potassium permanganate. FIG. 6C depicts the spectra of a porcine intestinal heparin sulfate enriched in reducing end N-acetylglucosamine residues (PI-HSNAc). FIG. 6D depicts the spectra of the porcine intestinal heparin sulfate enriched in reducing end N-acetylglucosamine residues after oxidation with potassium permanganate (PI-HSNAc$_{ox}$).

Figure 7A:
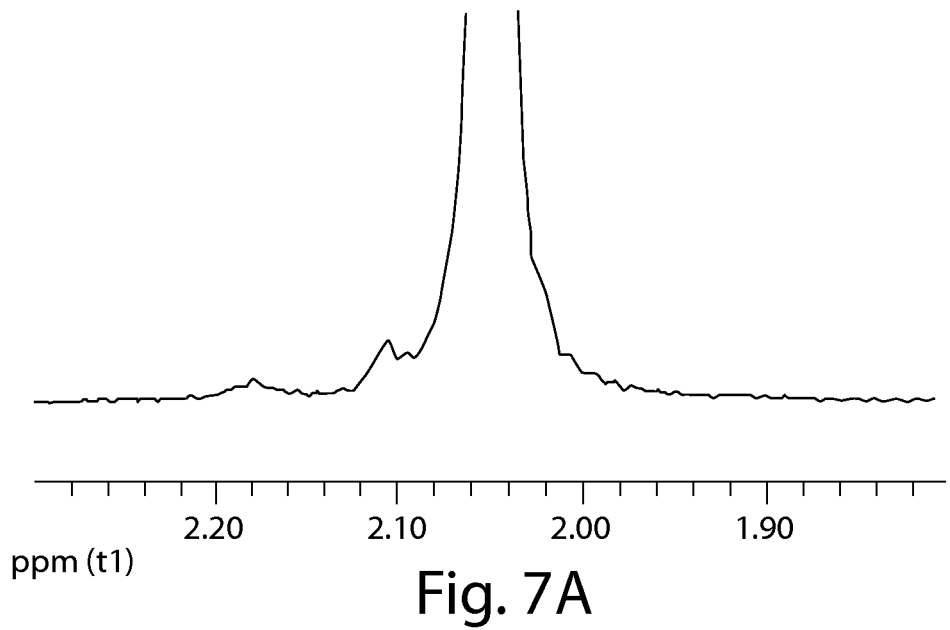
Figure 7B:
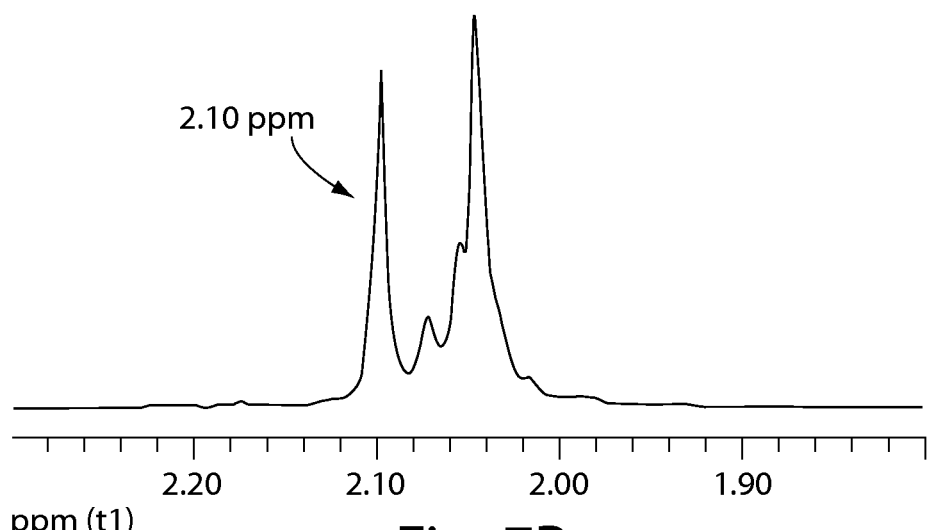
Figure 8A:
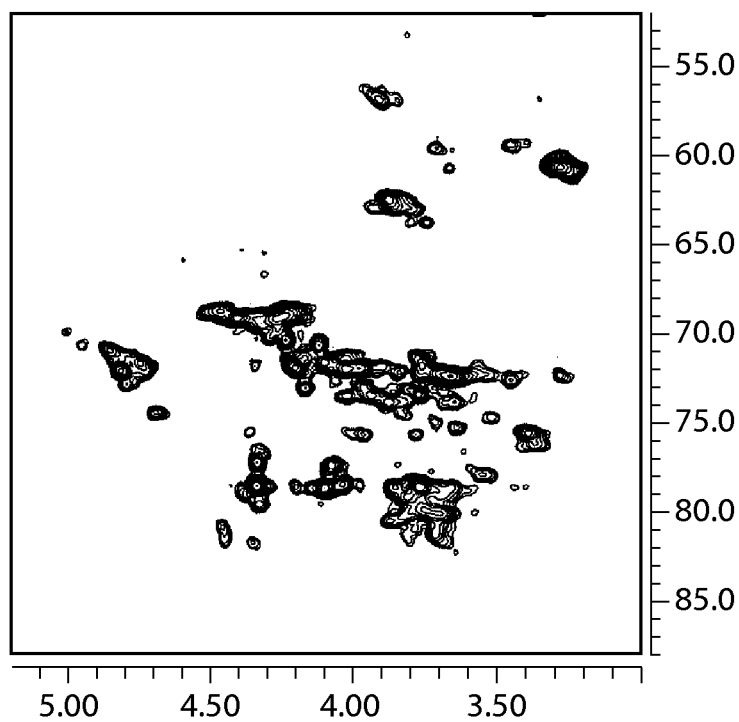
Figure 8B:
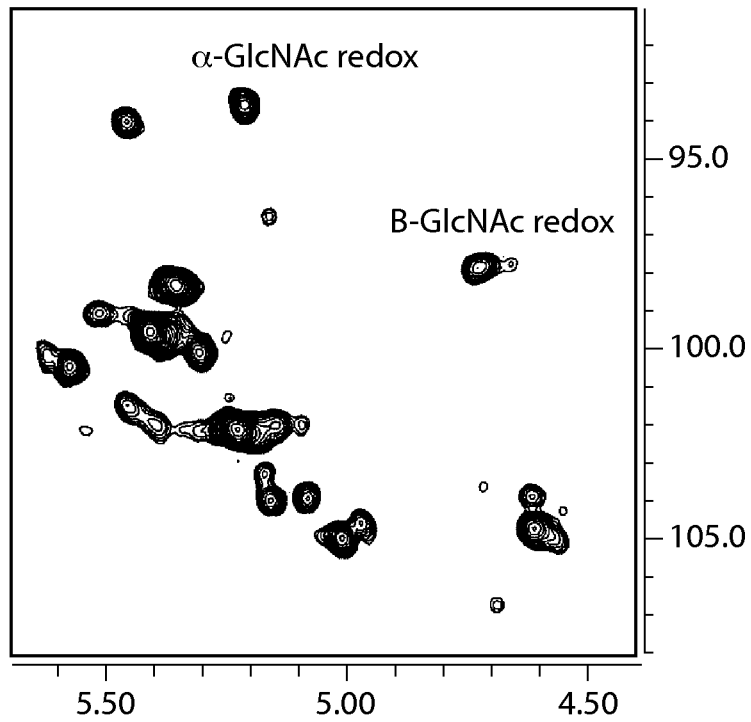
Figure 8C:
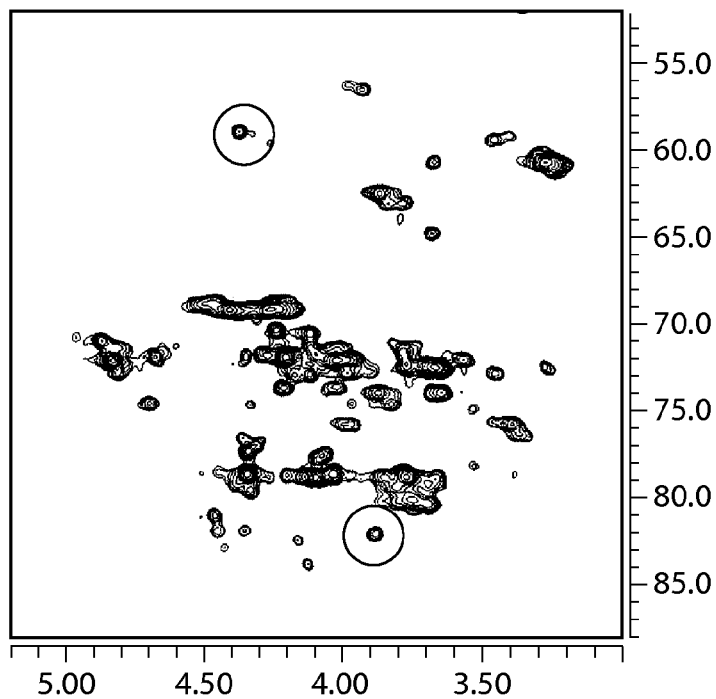
Figure 8D:
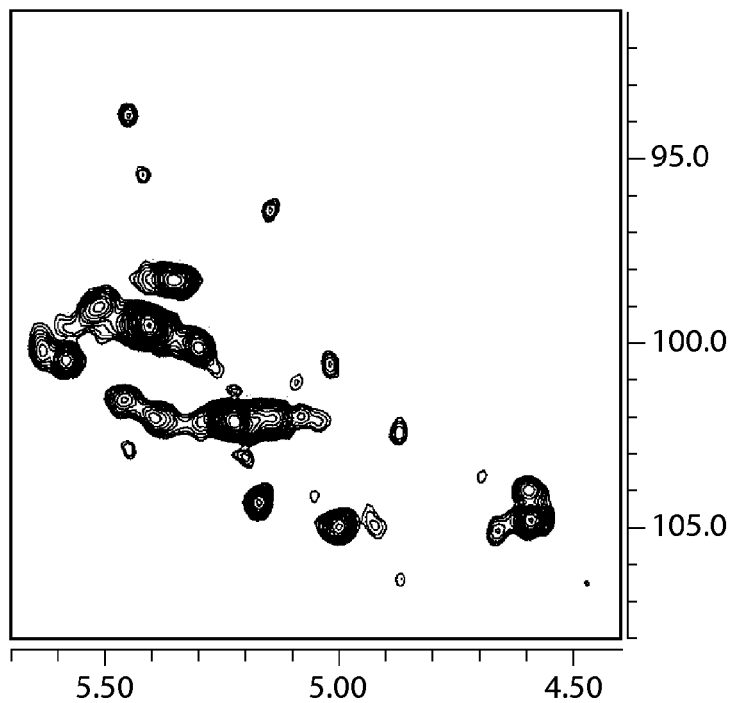

FIG. 7 depicts an expanded $^1$H 1D-NMR spectra of a LMWH with high percentage of GlcNAc at the reducing end of the chain before and after treatment with potassium permanganate. FIG. 7A depicts the spectra of the starting LMWH. FIG. 7B depicts the spectra of LMWH after oxidation with potassium permanganate. The signal at 2.10 ppm is labeled and is greatly increased in this sample.

FIG. 8 depicts 2D-NMR(HSQC) spectra of a heparan sulfate preparation with high percentage of GlcNAc at the reducing end of the chain before and after treatment with potassium permanganate. FIG. 8A depicts 2D-NMR(HSQC) spectra of a heparan sulfate preparation with a high percentage of GlcNAc at the reducing end of the chain before oxidation with potassium permanganate. FIG. 8B depicts the 2D-NMR (HSQC) spectra of a starting PI-HSNAc preparation. FIG. 8C depicts a 2D-NMR(HSQC) spectra of a heparan sulfate preparation with high percentage of GlcNAc at the reducing end of the chain; and shows the appearance of two distinct cross peaks at 4.37/58.9 ppm and 3.88/81.8 ppm after potassium permanganate oxidation. The signals arising from the reducing end GlcNAc are labeled. FIG. 8D depicts the 2D-NMR(HSQC) spectra of the heparin sulfate preparation after oxidation with potassium permanganate (PI-HSNAc$_{ox}$).

Figure 9:
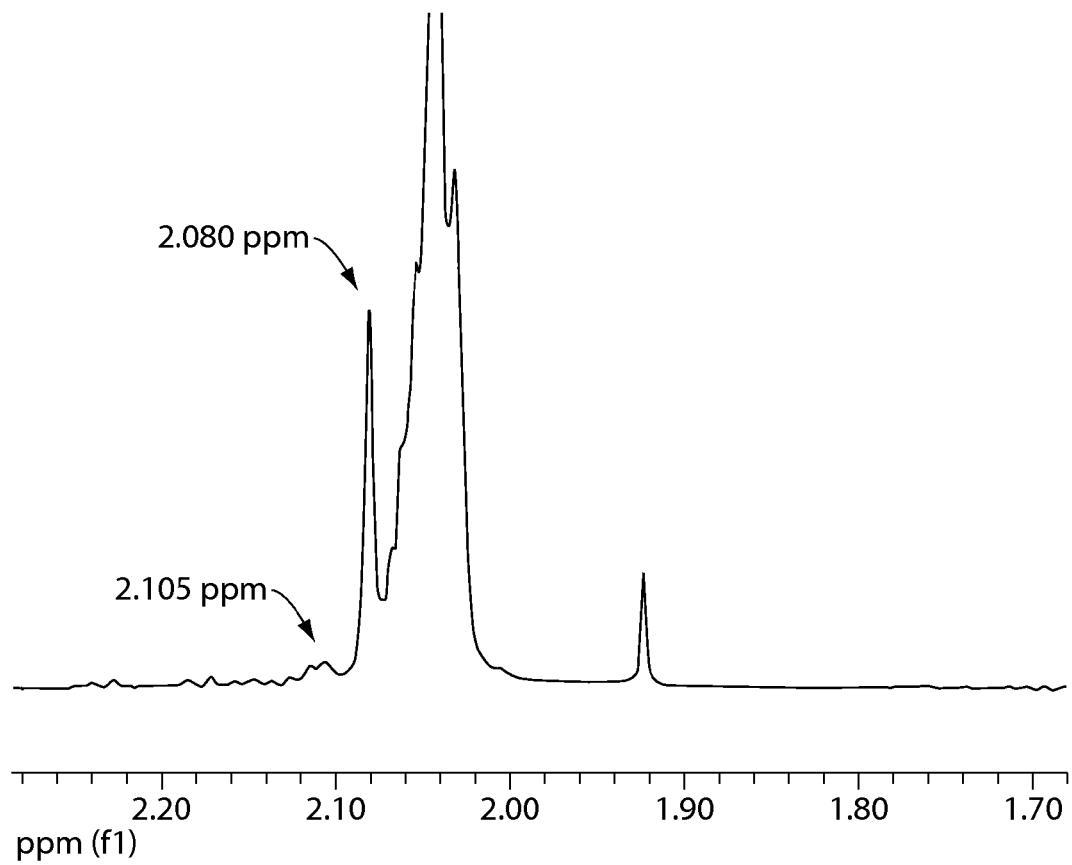

FIG. 9 depicts an expanded $^1$H 1D-NMR spectra of a heparin preparation subjected to periodate oxidation and subsequent acidic treatment.

Figure 10A:
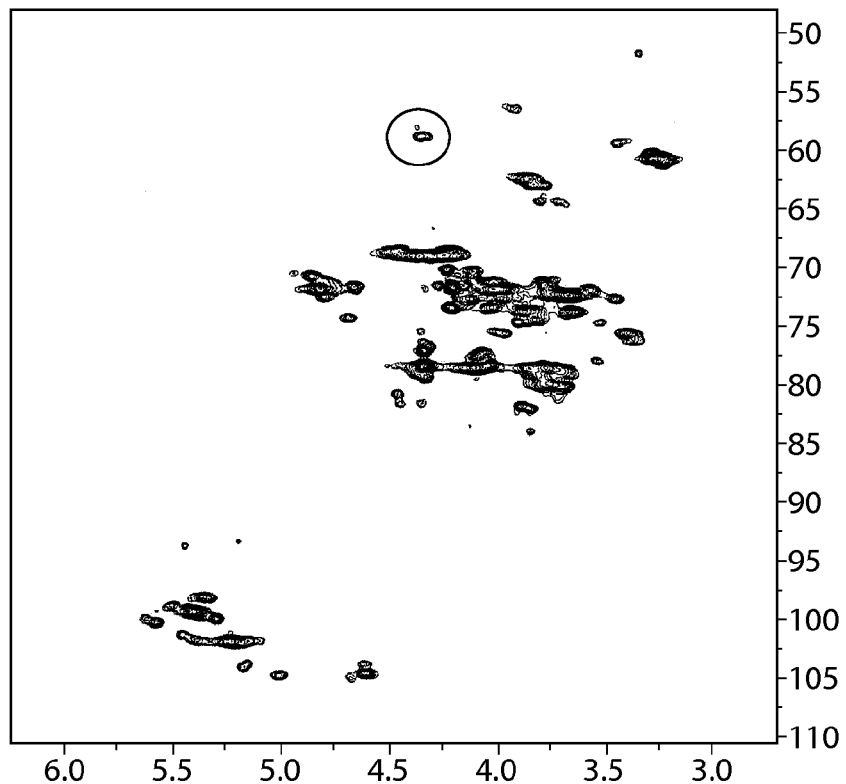
Figure 10B:
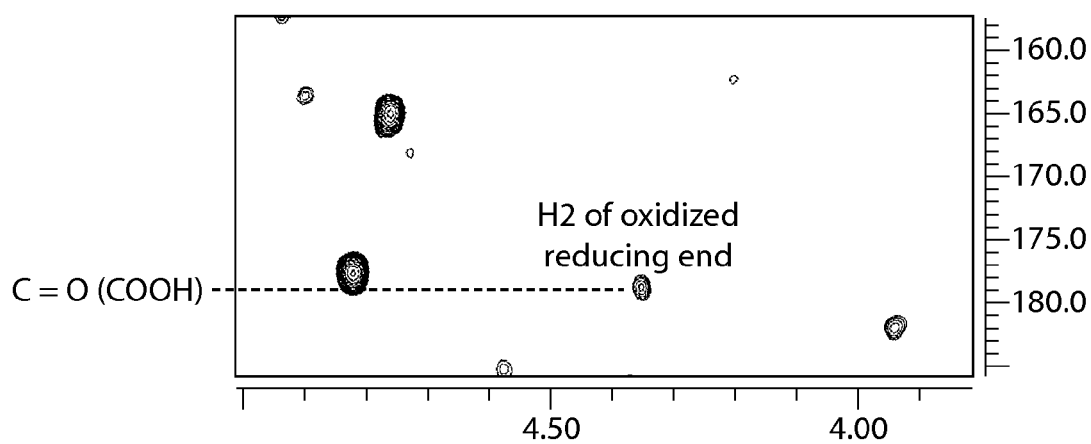

FIG. 10 depicts a 2D-NMR spectra of PI-HSNAc$_{ox}$. FIG. 10A is a HSQC-DEPT spectra of PI-HSNAc$_{ox}$. The CH cross peaks are shown in the boxes. The cross peak at 4.37/58.9 ppm is highlighted. FIG. 10B is a HMBC spectra of PI-HSNAc$_{ox}$. The long-range correlation between proton 4.37 ppm and a carbonyl group is indicated.

Figure 11A:
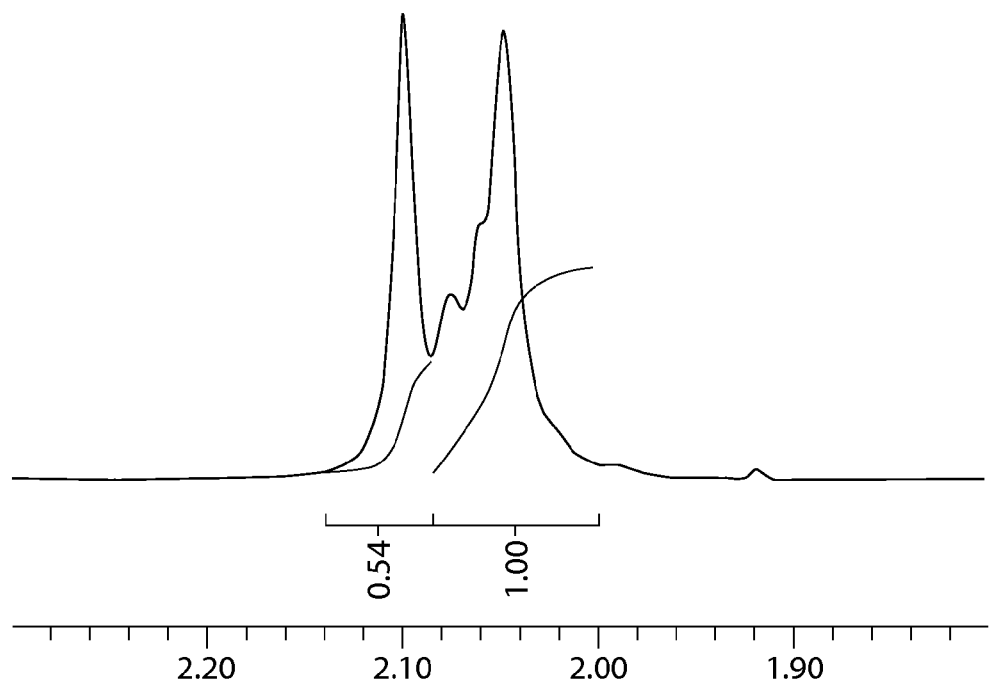
Figure 11B:
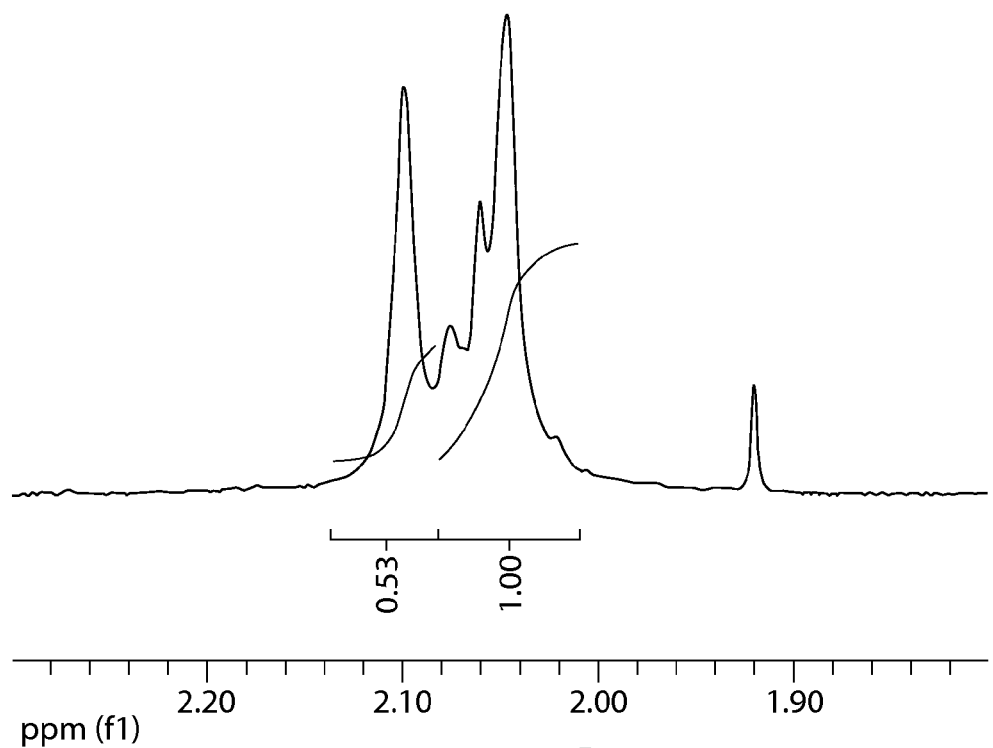

FIG. 11 depicts a 1D-NMR spectra of PI-HSNAc$_{ox}$. FIG. 11A depicts the 1D-NMR spectra of PI-HSNAc$_{ox}$. FIG. 11B depicts the spectra of PI-HSNAc$_{ox}$ after treatment with sodium borodeuteride and neutralization.

Figure 12A:
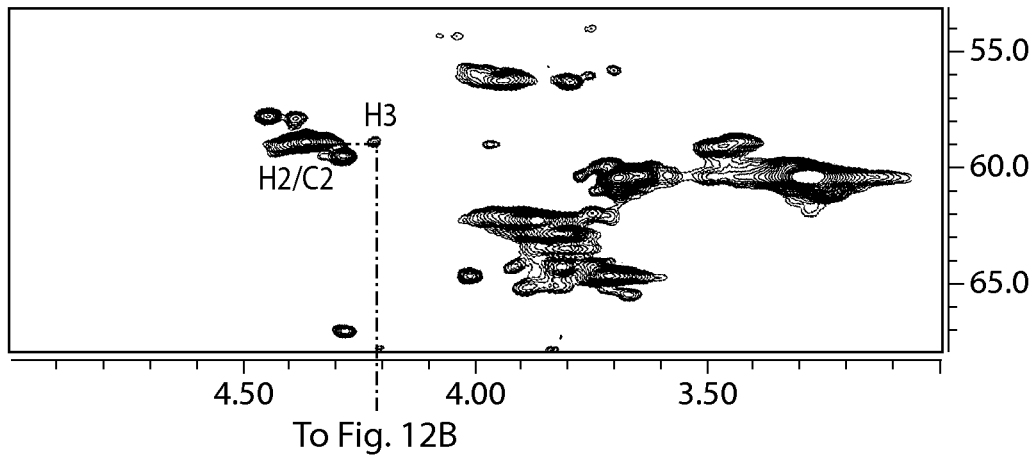
Figure 12B:
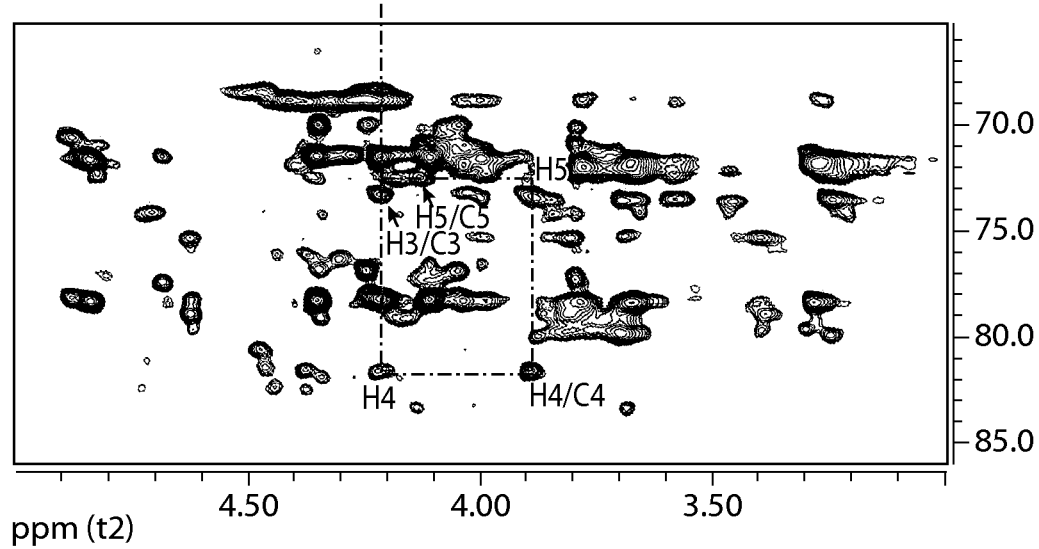

FIG. 12 depicts a 2D-NMR spectra of PI-HSNAc$_{ox}$. FIG. 12A depicts the HSQC-TOSCY spectra of PI-HSNAc$_{ox}$ recorded with a 20 ms mixing time. FIG. 12B depicts the HSQC-TOSCY spectra of PI-HSNAc$_{ox}$ recorded with a 90 ms mixing time.

Figure 13:
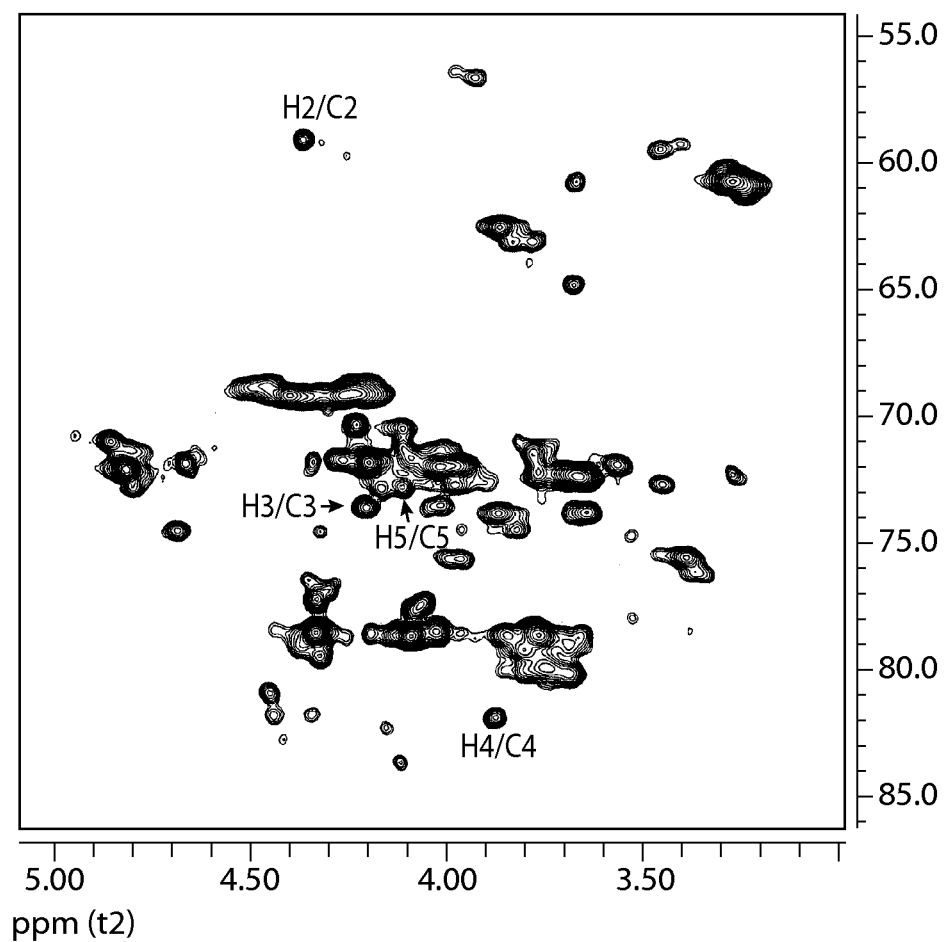

FIG. 13 depicts an HSQC spectra of PI-HSNAc$_{ox}$. NMR assignments for the oxidized residues are indicated close to the relative contours.

Figure 14:
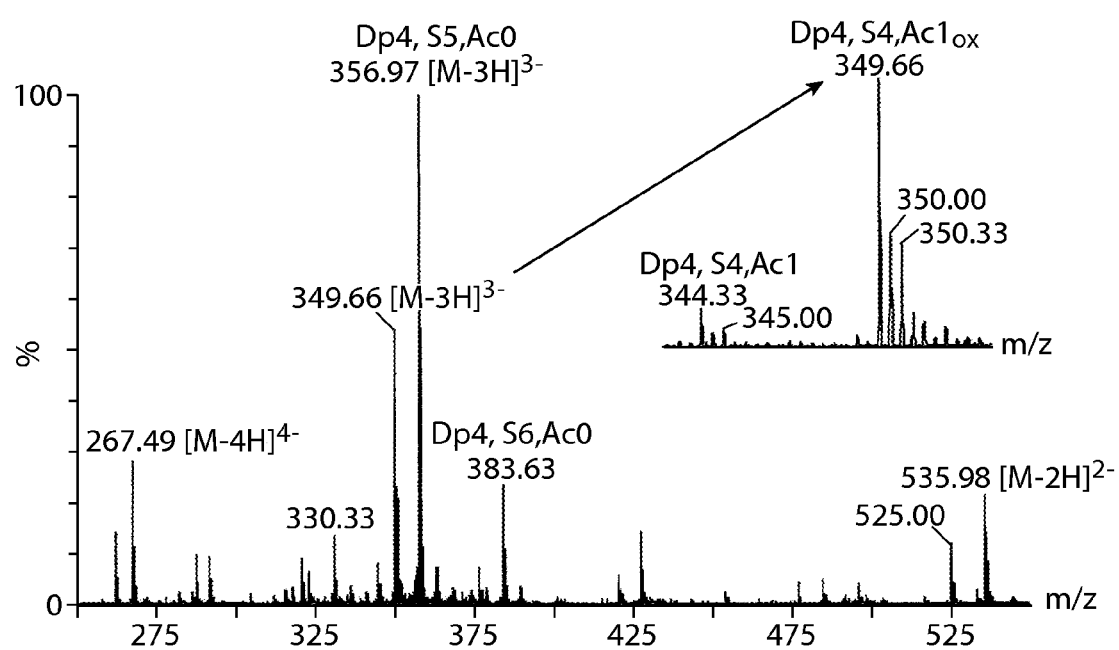

FIG. 14 depicts a negative-ion ESI-MS spectrum of the oxidized tetrasaccharide species containing four sulfates and one acetyl group (Dp4, S4, Ac1$_{ox}$).The insert shows the well resolved isotopic peaks of oxidized tetrasaccharide.

Figure 15A:
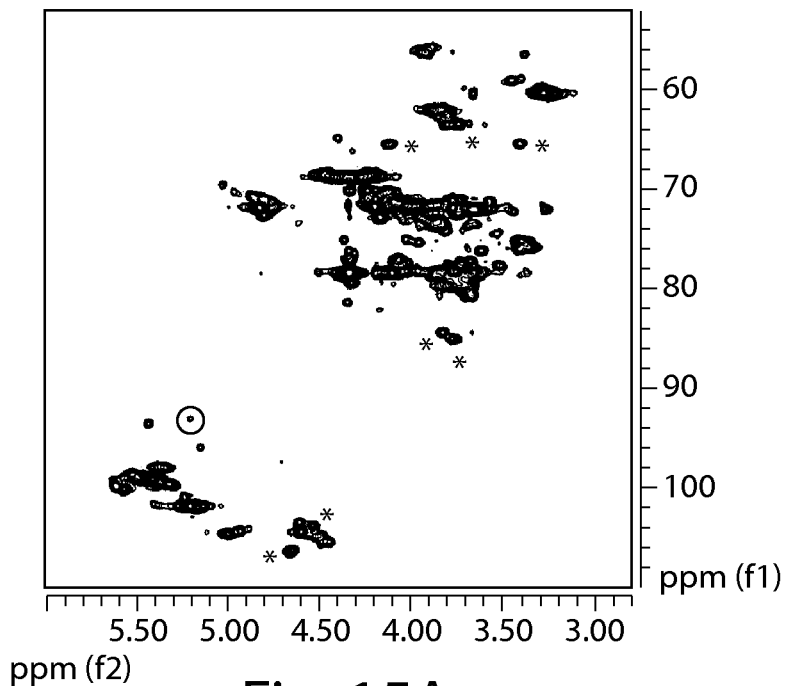
Figure 15B:
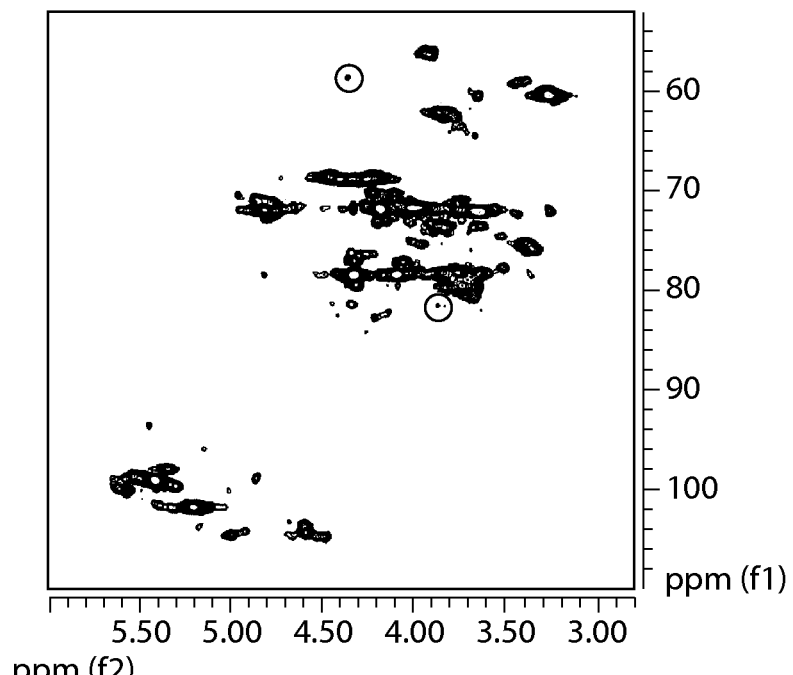

FIG. 15 depicts a 2D-NMR spectra of an unfractionated heparin preparation. FIG. 15A depicts the spectra of an unfractionated heparin preparation that has not been oxidized. FIG. 15B depicts the unfractionated heparin preparation treated with KMnO$_4$. The H1/C1 signal of GlcNAc a reducing end disappeared, while signals at 4.37/58.9 and 3.88/81.8 appeared (see circled signals). Signals due to linkage region (indicated with * in A are also missing.

Figure 16:
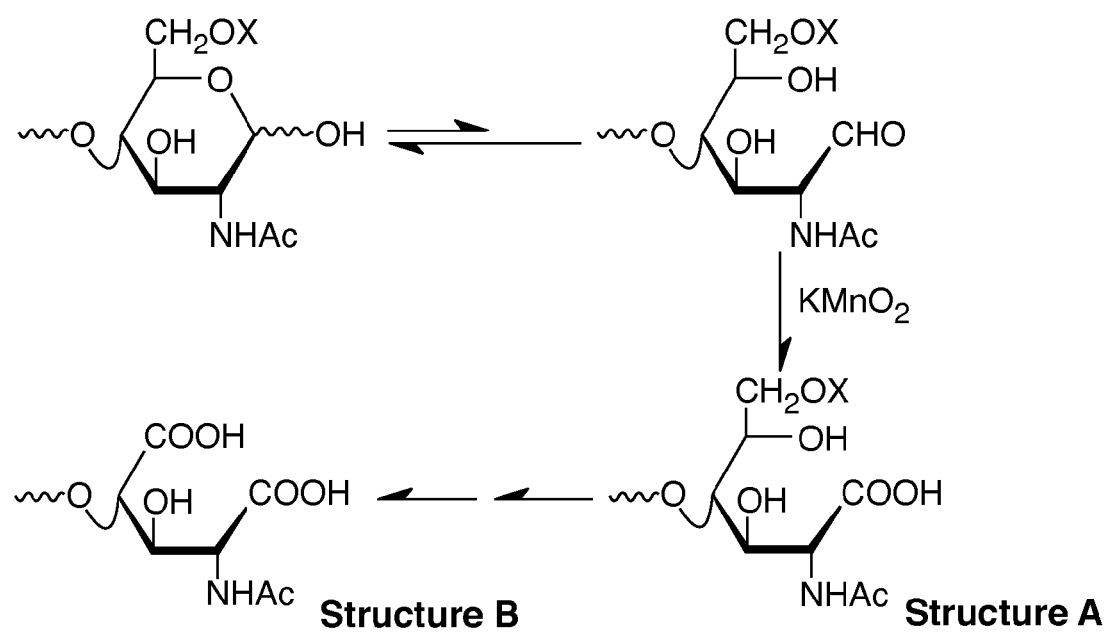

FIG. 16 depicts a reaction scheme outlining the formation of structure A (N-acetylglucosaminic acid; where X=H or SO3) generated as a result of potassium permanganate oxidation at the reducing end of chains. It is possible that further oxidation of structure A (if X=H) may result in the formation of a dicarboxylic acid (Structure B).

DETAILED DESCRIPTION

The disclosure is based, at least in part, on the finding that peaks within the N-acetyl region of a $^1$H 1D-NMR spectra of a heparin preparation are associated with characteristic structural signatures which reflect the process used to make the heparin preparation. For example, the presence of a peak at 2.10 ppm in a $^1$H 1D-NMR spectra of unfractionated heparin represents a characteristic structural signature that is reflective of an oxidative processing step in the manufacture of unfractionated heparin. As another example, an increased amount of a structural signature associated with a peak at 2.08 ppm of a $^1$H 1D-NMR spectra indicates an oxidized heparin preparation that has been subjected to acid treatment. Therefore, in some embodiments, a method described herein can include evaluating the absence, presence or amount of a structural signature associated with a peak in the N-acetyl region of a $^1$H 1D-NMR spectra of a heparin preparation. The N-acetyl region refers to a region from about 1.8 ppm to 2.20 ppm, e.g., 1.9 ppm to 2.15 ppm, 2.0 ppm to 2.12 ppm, 2.02 ppm to 2.10 ppm of a $^1$H 1D-NMR spectra. Presence means whether a structural signature can be detected. Amount refers to the amount, e.g., as % by weight or number.

In some embodiments, a method described herein can be used to determine if a heparin preparation (e.g., an unfractionated heparin preparation or a low molecular weight heparin (LMWH) preparation) is at risk for coloration. Some heparin preparations have limited shelf life due, at least in part, to the development of color is the preparation during storage. The phrase coloration means greater than 0.2 absorbance units in an accelerated stability test such as the calorimetric analysis described in U.S. Publication no.: 20080318328.

As used herein, "acquiring a value" refers to any process that results in possession of the value. In an embodiment, acquiring a value comprises subjecting a sample to a process which results in a physical change in the sample or another substance, e.g., an analytical reagent or a device used in the analysis. Such methods comprise analytical methods, e.g., a method which include one or more of the following: separating a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment of other derivative thereof, e.g., by breaking or forming a covalent or non covalent bond, between a first and a second atom of the analyte. Typical analytical methods include high performance liquid chromatography (HPLC), nuclear magnetic resonance (NMR), capillary electrophoresis (CE) and mass spectroscopy (e.g., matrix-assisted laser desorption ionization-mass spectroscopy (MALDI-MS), electrospray ionization-mass spectroscopy (ESI-MS)), and fast protein liquid chromatography (FPLC).

In an embodiment, a party that practices the method performs the process. As used herein, "directly acquiring," refers to a process in which the party that practices the method performs the process. In an embodiment, a party that practices the method receives the value from another party. As used herein, "indirectly acquiring," refers to a process in which the party that practices the method receives the value from another party. Typically, even in embodiments characterized by indirect acquisition, some party has subjected a sample to a process as described above that results in a physical change in the sample or another substance. In an embodiment, a party that practices the method of evaluating instructs another party to perform the process, and e.g., a party that practices the method receives the value.

Heparin Preparations

A heparin preparation, as used herein, is a preparation which contains heparin or a preparation derived there from, and thus includes unfractionated heparin, low molecular weight heparin (LMWH), ultra low molecular weight heparin (ULMWH) and the like.

The term "unfractionated heparin (UFH)" as used herein, is heparin purified from porcine intestinal mucosa. UFH can be used, e.g., as a starting material in the process to form a LMWH. Unfractionated heparin is commercially available from several vendors including Abbott, Organon, Riker, Invenex, Baxter, Calbiochem, Sigma or Upjohn. In some embodiments, the heparin is made by a process that includes an oxidation step. The oxidation step can include using at least one of: a permanganate salt peroxide, periodate, chlorine, chlorine dioxide, and combinations thereof. For example, the permanganate salt can be one or more of potassium permanganate, sodium permanganate, quaternary ammonium permanganate, hydrogen peroxide. Preferably, the oxidation step includes using a permanganate salt. In some embodiments, the heparin is made by a process that includes a reduction step, e.g., such as treatment with sodium borohydride, lithium aluminum hydride, or combinations thereof.

The heparin preparation can also be a LMWH preparation. Examples of LMWH preparations include, but are not limited to, an enoxaparin preparation (Lovenox™ or Clexane™); a dalteparin preparation (Fragmin™); a certoparin preparation (Sandoparin™ or Embollex); an ardeparin preparation (Normiflo™); a nadroparin preparation (Fraxiparin™); a parnaparin preparation (Fluxum™); a reviparin preparation (Clivarin™); a tinzaparin preparation (Innohep™ or Logiparin™), a fondaparinux preparation (Arixtra™), or a M118-REH preparation. In some embodiments, the LWMH preparation can be a LMWH preparation made by one or more of the following methods: fractionation using solvents (French Patent No.: 2,440,376, U.S. Pat. No. 4,692,435); fractionation using an anionic resin (French Patent No.: 2,453,875); gel filtration (Barrowcliffe (1977) Thromb. Res. 12:27-36); affinity chromatography (U.S. Pat. No. 4,401,758); controlled depolymerization by means of a chemical agent including, but not limited to, nitrous acid (European Patent No.: 014 184 B1, European Patent No.: 037 319 B1, European Patent No.: 076 279 B1, European Patent No.: 623 629 B1, French Patent No.: 2,503,714, U.S. Pat. No. 4,804,652 and PCT Publication No.: WO 81/03276), beta-elimination from a heparin ester (European Patent No.: 040 144 B1, U.S. Pat. No. 5,389,618), periodate (EP 287477), sodium borohydride (EP 347588, EP 380943), ascorbic acid (U.S. Pat. No. 4,533,549), hydrogen peroxide (U.S. Pat. No. 4,629,699, U.S. Pat. No. 4,791,195), quaternary ammonium hydroxide from a quaternary ammonium salt of heparin (U.S. Pat. No. 4,981,955), alkali metal hydroxide (European Patent No.: 380 943, European Patent No.: 347 588), by an enzymatic route (European Patent No.: 064 452, U.S. Pat. No. 4,396,762, European Patent No.: 244 235, European Patent No.: 244 236; U.S. Pat. No. 4,826,827; U.S. Pat. No. 3,766, 167), by means of irradiation (European Patent No.: 269 981), and other methods or combinations of methods such as those described in U.S. Pat. No. 4,303,651, U.S. Pat. No. 4,757,057, U.S. Publication No.: 2007/287683, PCT Publication No.: WO 2009/059284 and PCT Publication No.: WO 2009/059283.

In some embodiments, a heparin preparation, e.g., an unfractionated heparin preparation, can be selected for further processing based upon the absence, presence or amount of a structural signature that indicates the method used to make the heparin preparation. For example, an unfractionated heparin preparation can be selected for further processing, e.g., into a LMWH preparation. The unfractionated heparin preparation can be selected for further processing, e.g., by one or more of the methods described above.

Database

Figure 1A:
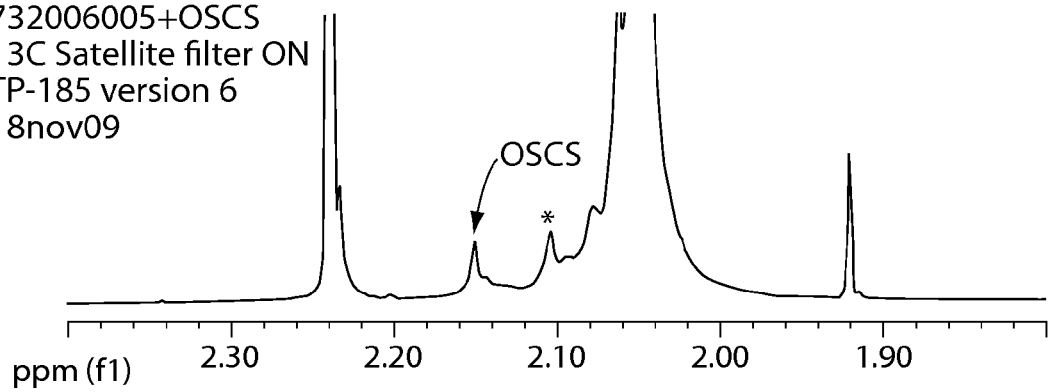
Figure 1B:
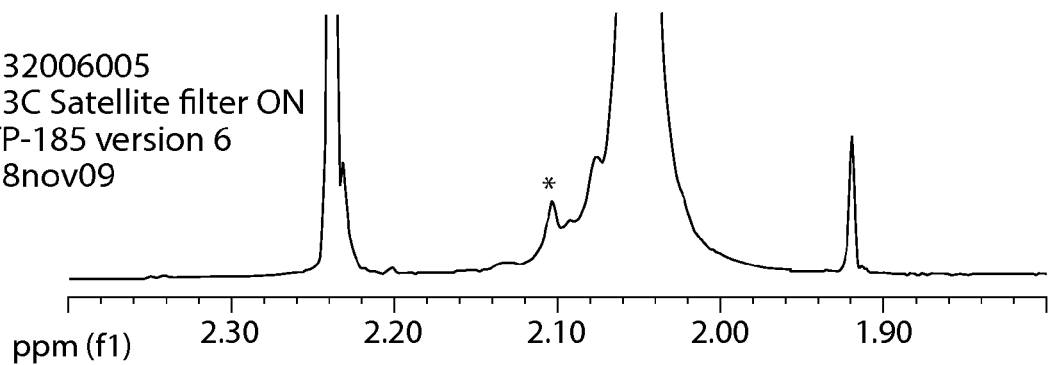

The disclosure also features a database that correlates the presence or amount of a structural signature associated with a peak in the N-acetyl region of a $^1$H 1D-NMR spectra, e.g., a peak at 2.08 ppm of FIG. 9 and/or the peak at 2.10 ppm of FIG. 1, with a method used to make the heparin preparation (e.g., a method that includes oxidation or oxidation followed by treatment with an acid), and use of such a database, e.g., in a method described herein. The term "database" refers to a collection of data. Typically, it is organized so that its contents can easily be accessed, managed, and updated. In one embodiment, the database is configured or managed to ensure its integrity and quality, to minimize content beyond records described herein, and to allow controlled access. The database is presented or memorialized on a medium. The medium can be, e.g., a traditional paper medium or other medium which displays printed or written symbols which can be directly (e.g., without the aid of a computer) used by a human being. Such a database can exist as a set of printed tables, or a card catalogue, which, e.g., show the relationship of the structural signature to the method used to produce the heparin preparation. The database can also be presented or memorialized in electronic or other computer readable form. These embodiments can range from simple spreadsheets to more complex embodiments. The database need not be deposited on a single unit of medium, e.g., in a single table or book, or on a single computer or network. A database, e.g., can combine a traditional medium as described above with a computer-readable medium. Typically, the database will contain a collection of records, wherein each record relates a structural signature to a method of manufacture by way of a correlative function. The database can be organized in a number of ways, e.g., as a relational database. Typically the database is in a format that can be searched for specific information or records by techniques specific to each database. A computer database is typically a structured collection of records stored in a computer or computers so that a program can consult it to answer queries.

Reference Values and Standards

A reference standard, by way of example, can be a value determined from a reference heparin preparation (e.g., a commercially available heparin preparation or a heparin preparation made by a particular method). For example, a reference standard can be a value for the presence of a structural signature in a preparation, e.g., a reference heparin preparation. The reference standard can be numerical or non-numerical, e.g., it can be a qualitative value, e.g., yes or no, or present or not present at a preselected level of detection, or graphic or pictorial. The reference standard can also be values for the presence of more than one structural signature in a sample. For example, the reference standard can be a map of structures (e.g., structures associated with peaks in the N-acetyl region of $^1$H-1D-NMR spectra) present in a heparin preparation when analyzed by a separation method described herein. The reference standard can also be a release standard (a release standard is a standard which should be met to allow commercial sale of a product) or production standard, e.g., a standard which is imposed, e.g., by a party, e.g., the FDA, on a heparin or LMWH.

Detection of Structural Signatures

The absence, presence or amount of a structural signature associated with a peak in the N-acetyl region of a $^1$H 1D-NMR spectra can be determined by any separation method that allows for identification of the structural signature in a heparin preparation. For example, one or more of the following separation methods can be used: high performance liquid chromatography (HPLC), nuclear magnetic resonance (NMR), capillary electrophoresis (CE) and mass spectroscopy (e.g., matrix-assisted laser desorption ionization-mass spectroscopy (MALDI-MS), electrospray ionization-mass spectroscopy (ESI-MS)), and fast protein liquid chromatography (FPLC).

In one embodiment, the absence, presence or amount of a structural signature is determined using 1D-NMR or 2D-NMR. The 2D-NMR can be carried out using homonuclear (e.g., COSY, TOCSY, NOESY and ROESY) and/or heteronuclear (e.g., HSQC, HSQC-DEPT, HMQC-COSY, HSQC-TOSCY and HMBC) spectroscopy. The peaks depicted in many of the Figures were obtained using $^1$H 1D-NMR. The general procedure for the $^1$H 1D-NMR was as follows: an unfractionated heparin sample (approximately 20 mg) was dissolved in 0.7 ml of $D_2O$ (deuterium oxide, 99.96% atom D) and transferred to a 5 mm NMR tube. Proton ($^1$H) 1D-NMR spectra were acquired on a 600 MHz Varian VNMRS spectrometer equipped with a 5 mm triple resonance probe. Data were acquired at 25° C., with presaturation of the water signal, for 16-32 scans and a 10 second delay. The NMR spectrum was collected with a spectral window of 14 to -2 ppm. Samples were calibrated either using an added internal standard (0.1% w/v TSP; methyl protons set at 0.00 ppm), or by setting the major N-acetyl methyl proton signal of heparin to 2.045 ppm.

The initial experiments performed confirmed that a peak at 2.10 ppm is not over sulfated chondrotin sulfate (OSCS), a contaminant sometimes found in heparin. The results indicated that OSCS shows a major distinct peak at 2.15 ppm that is well resolved from the peak at 2.10 ppm (FIG. 1).

Figure 2:
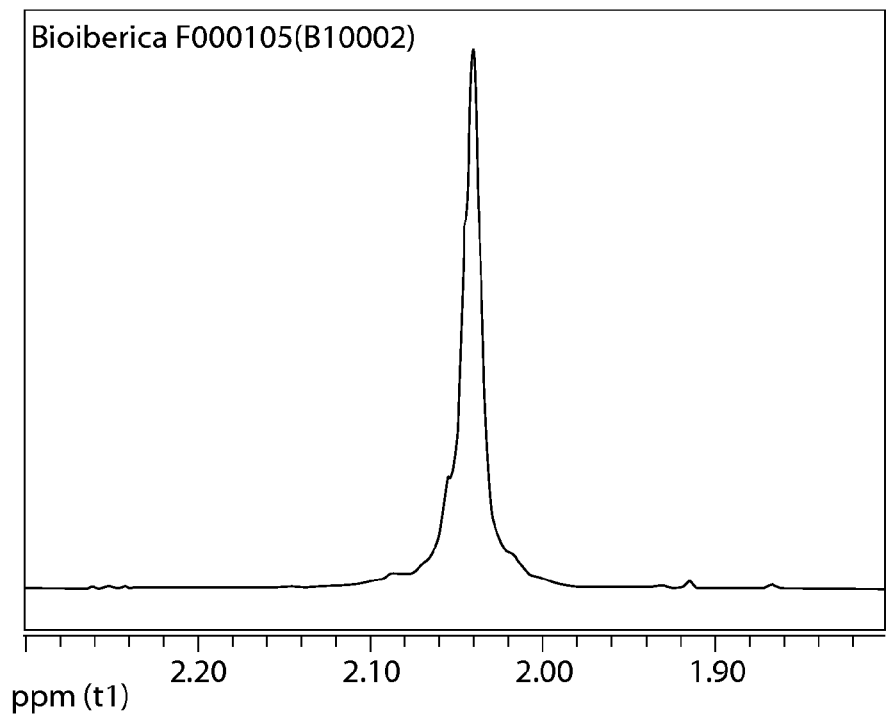
FIG. 2 depicts an expanded $^1$H 1D-NMR spectra of an unfractionated heparin sodium manufactured using process A (which does not include an oxidative processing step).
Figure 3:
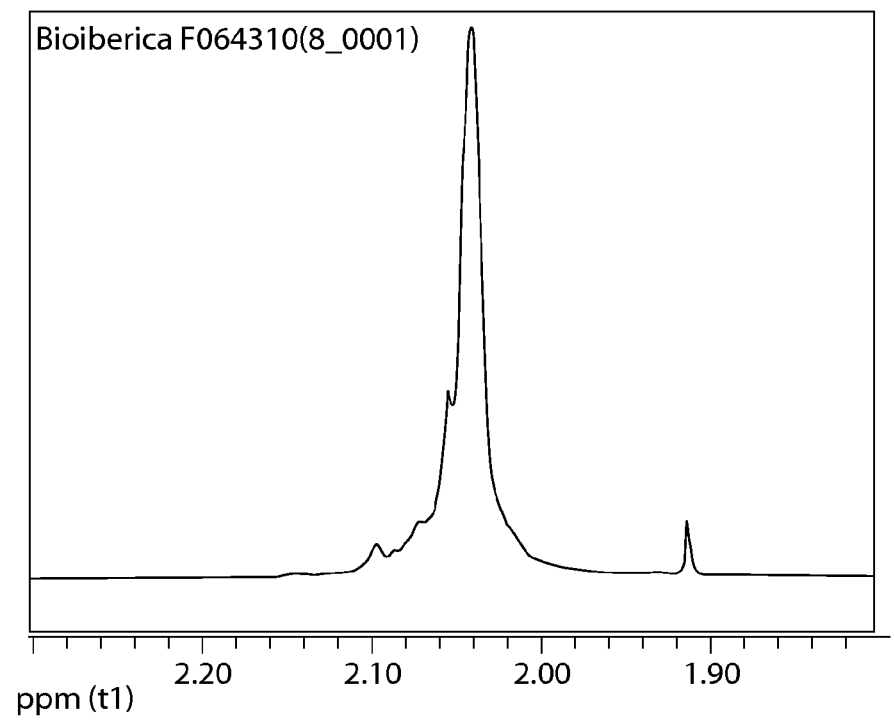
FIG. 3 depicts an expanded $^1$H 1D-NMR spectra of an unfractionated heparin sodium manufactured using process B (which includes an oxidative processing step) with the presence of the signal at 2.10 ppm.

NMR was also used to analyze unfractionated heparin preparations obtained from different sources to understand the potential origin of the peak at 2.10 ppm. FIG. 2 shows an unfractionated heparin preparation made by process A and which does not contain the signal at 2.10 ppm, whereas FIG. 3 shows an unfractionated heparin preparation made by a different process, process B, and which does contain the signal at 2.10 ppm. This indicates that the different processing conditions can have an effect on observation of the peak at 2.10 ppm. The unfractionated heparin preparation analyzed in FIG. 3 underwent an oxidative processing step (process B), whereas the unfractionated heparin preparation analyzed in FIG. 2 did not undergo an oxidative processing step (process A). Thus, the peak at 2.10 ppm observed in the $^1$H 1D-NMR of unfractionated heparin arises due to oxidative processes that the heparin has been subjected to during manufacturing. This oxidative processing modifies the chemical environment around the N-acetylglucosamine residue, thereby giving rise to the peak at 2.10 ppm.

Based on these initial observations, a low molecular weight heparin (LMWH) preparation that had been subjected to an oxidative process was evaluated. $^1$H 1D-NMR data obtained on intermediates from a process used to make a LMWH preparation indicated that oxidation with sodium periodate yielded a LMWH preparation that shows the appearance of signals in the 2.10 ppm region. In FIG. 5, the top panel shows the starting LMWH sample (Intermediate 1 which has not been subjected to oxidation and which does not have a detectable signal at 2.10 ppm. This LMWH intermediate was subjected to oxidation with sodium periodate. After oxidation, the resulting LMWH preparation, (Intermediate 2; bottom panel of FIG. 5), showed the presence of signals at 2.09 and 2.10 ppm. The presence of these signals is likely due to a change in the environment of the N-acetyl groups present on the glucosamine residues adjoining the uronic acid residues in heparin that have been oxidized as a result of periodate treatment. It is also worth noting that agents like permanganate follow similar mechanisms of oxidation, and permanganate is commonly used in heparin oxidation processes during purification.

Further experiments were performed to determine whether a modification on or near the N-acetylglucosamine (GlcNAc) residue occurred when the residue was present internally within the chain, or at the reducing end of the chain. To test this, a preparation of porcine intestinal heparan sulfate with a high number of chains having an internal GlcNAc (PI-HS) was subjected to oxidation with potassium permanganate (PI-HS$_{ox}$). In conjunction, a sample of porcine intestinal heparan sulfate enriched in reducing end N-acetylglucosamine residues (PI-HSNAc) was prepared and subjected to the same oxidation with potassium permanganate (PI-HSNAc$_{ox}$) as the porcine intestinal heparin sulfate.

In addition, a low molecular weight heparin preparation prepared by enzymatic digestion that has a high percentage of GlcNAc at the reducing ends of the chains in the sample was subjected to permanganate oxidation. Both preparations were subjected to the same oxidation conditions.

The results from these experiments are shown in FIGS. 6 and 7. Oxidation of the heparan sulfate preparation with permanganate resulted in a very small increase of the peak at 2.10 ppm (FIG. 6B). In contrast, the heparin sulfate preparation enriched in reducing end N-acetylglucosamine was oxidized, there was an intense signal at 2.10 ppm (FIG. 6D), indicating that the oxidative chemistry had a significant influence on the N-acetylglucosamine residues at the reducing end position of the heparin chain. In addition, when the LMWH preparation that has a high percentage of GlcNAc at the reducing end was oxidized, there was a dramatic increase in the peak at 2.10 ppm (FIG. 7). These results suggest that the structure resulting in the peak at 2.10 ppm arises from N-acetylglucosamine at or near the reducing end of the chain.

These experiments demonstrate that signals in the N-acetyl region of the $^1$H 1D-NMR spectra of unfractionated heparins can be indicative of different processing steps undertaken during the manufacture of heparin.

The presence of reducing α and β N-acetylglucosamine residues in PI-HSNAc and PI-HSNAc$_{ox}$ was confirmed by multidimensional experiments, i.e., COSY, TOCSY and HSQC. The HSQC spectra showed that after oxidation, the signals arising from GlcNAc at the reducing end are no longer observed (FIG. 8). Comparison between HSQC spectra of PI-HSNAc (FIG. 8B) and PI-HSNAc$_{ox}$ (FIG. 8D) demonstrate that signals due to reducing α and β anomeric signals of the reducing end N-acetylglucosamine residues disappeared after potassium permanganate treatment, while peaks due to internal N-acetylglucosamine (5.4-5.3/100.3-98.8 ppm) did not increase in intensity.

Concomitantly, two distinct cross peaks appear at 4.37/58.9 ppm and 3.88/81.8 ppm (FIG. 8C) after potassium permanganate oxidation. An HSQC-DEPT experiment assigned the peak at 4.37/58.9 ppm to a —CH residue (FIG. 10A). A COSY experiment recorded in 10% deuterated water showed a cross peak between an amide proton (from the N-acetyl group) at 7.99 ppm and the peak at 4.37 ppm, while a NOESY experiment acquired in 10% deuterated water correlated the amide proton at 7.99 ppm to the CH$_3$ signal at 2.10 ppm. These data suggest that the peak at 4.37 ppm arises due to the H2 of the oxidized N-acetylglucosamine residue. In addition, HMBC analysis showed a long-range correlation between the proton at 4.37/58.9 ppm and a carbonyl group (FIG. 10B). To determine if the carbonyl group belonged either to an aldehydic or carboxylic moiety, two experiments were performed. Firstly, the sample was acidified to pH 4.1 and an HSQC experiment was recorded. The experiment showed that the cross peak at 4.37/58.9 ppm shifted to 4.47/58.3 ppm as a function of the pH of the solution, consistent with a CH group adjacent to a carboxylic acid moiety. In addition, PI-HSNAc$_{ox}$ was treated with sodium borodeuteride (10% w/w) for 60 minutes at 4° C. and, after neutralization, was analyzed by $_1$HNMR (FIG. 11). The intensity of the signal at 2.10 ppm did not decrease after reduction, indicating that the methyl group of the oxidized N-acetylglucosamine residue is adjacent to a carboxylic acid group. Furthermore, COSY and TOCSY experiments do not show any correlation of this peak (4.37 ppm) with signals present in the anomeric region, indicating that C1 does not have a corresponding proton. This observation supports the assignment of the C1 as a carboxylic acid moiety.

HSQC-TOCSY experiments show additional correlations between the peak at 4.37/58.9 ppm and signals at 4.21/73.6 ppm, 3.88/81.8 ppm, and 4.12/72.8 ppm (FIG. 12). Assignment of these cross peaks was performed by analysis of HMQC-COSY and HSQC-TOCSY experiments recorded with different mixing times, and are reported in Table 1 below and in FIG. 13. Additional cross peaks at 3.80/64.4 ppm and 3.72/64.4 ppm were also observed in the HSQC spectra of all the samples treated with potassium permanganate. HSQC-DEPT spectra indicate that these signals arise from CH$_2$ moieties (FIG. 10A). Correlations between the peaks at 3.80 and 3.72 ppm and other protons of the oxidized residue could not clearly be identified by COSY and TOCSY experiments due to severe overlapping with other heparin signals. However, the proximity of the HSQC peaks at 3.80/64.4 ppm and 3.72/64.4 ppm to the H6,6'/C6 of 6-O-desulfated N-acetylglucosamine residues, and the appearance of these signals upon treatment with potassium permanganate, suggests assignment of these peaks to H6,6'/C6 of 6-O-desulfated N-acetylglucosaminic acid. The chemical shift assignments of the residue generated by potassium permanganate treatment are consistent with a 4-substituted N-acetylglucosaminic acid (Uchiyama et al. (1990) J. Biol. Chem., 265: 7753-7759).

TABLE 1

NMR assignment of the oxidized reducing end (N-acetylglucosaminic acid)

| | Heparin/Heparan Sulfate | |
|---|---|---|
| | $^1$H | $^{13}$C |
| C1 | — | 178.8 |
| H2/C2 | 4.37 | 58.9 |
| H3/C3 | 4.21 | 73.6 |
| H4/C4 | 3.88 | 81.8 |
| H5/C5 | 4.12 | 72.8 |
| H6, H6'/C6 | 3.80, 3.72* | 64.4* |

*These chemical shifts correspond to the residue that is non-sulfated at the 6-O position Based on these results, two possible structures that can give rise to the peak at 2.10 ppm have been determined. The structures are:

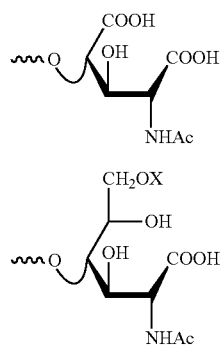

wherein, in structure B, X=H or SO$_3$.

Mass spectrometry was applied as an orthogonal analytical technique to support the structural assignment. The mass difference between N-acetylglucosamine and N-acetylglucosaminic acid at the reducing end is expected to be +16 Da. The PI-HSNAc$_{ox}$ sample was digested with Heparinase I and analyzed by gel permeation chromatography, followed by mass spectrometry.

The results showed that some acetylated species have 16 Da higher mass than the corresponding non-oxidized N-acetylglucosamine species (Supplementary FIG. 5). This observation further substantiates our claim of an oxidized —COOH moiety present at C1 of the reducing end N-acetylglucosamine.

Figure 6A:
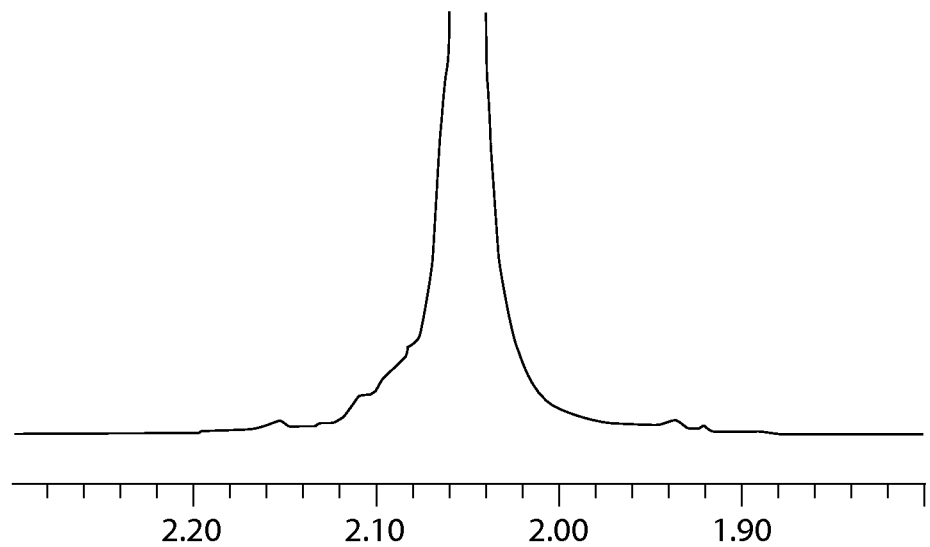
Figure 6B:
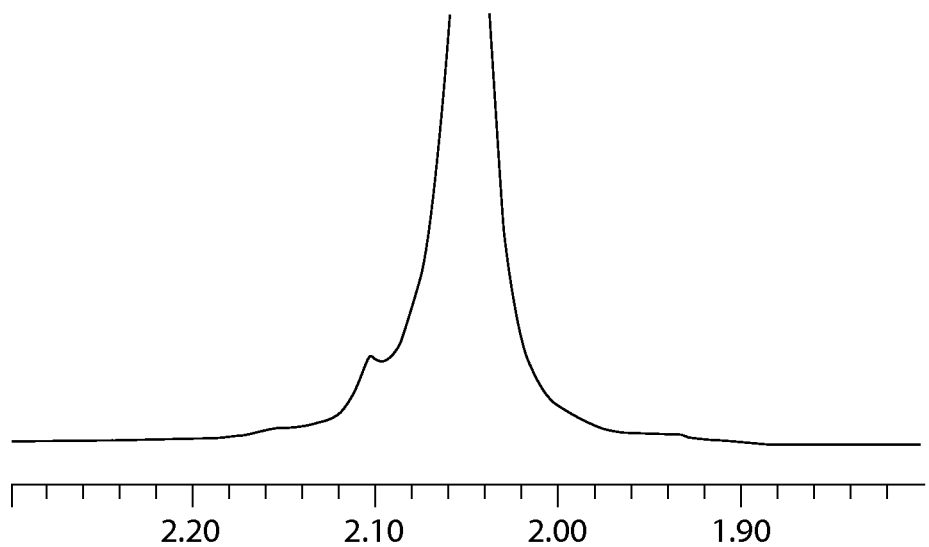
Figure 6C:
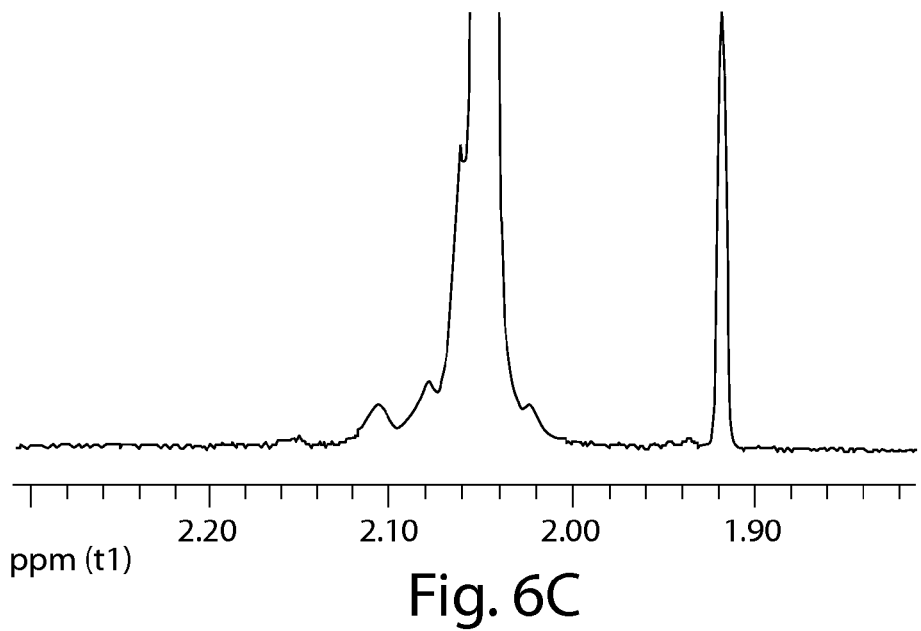
Figure 6D:
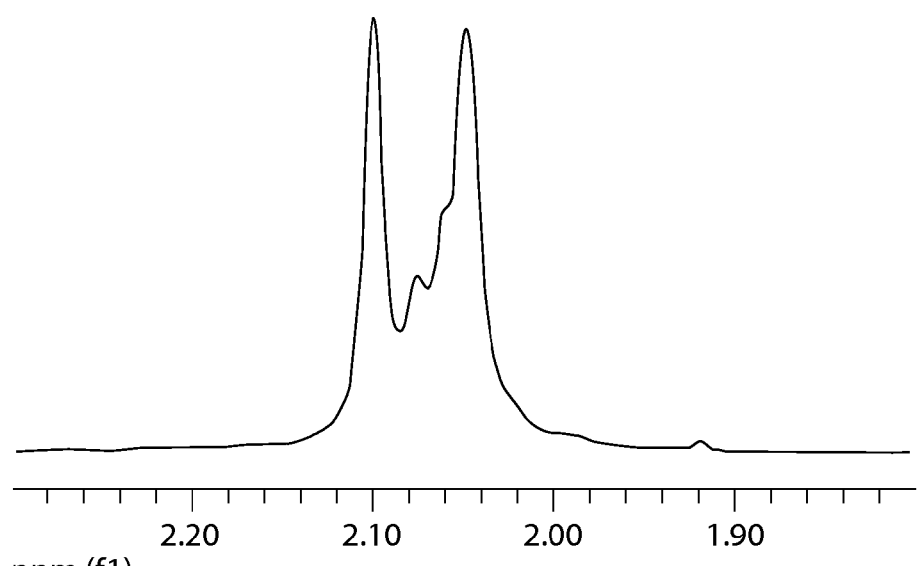

Finally, to confirm whether our observations on the model compound (PI-HSNAc) could be extended to unfractionated heparin, UFH lot 2 was subjected to oxidation with potassium permanganate. In unfractionated heparin samples the amount of N-acetylglucosamine at the reducing end is usually very low (below 1% of the total glucosamine content, as estimated by NMR). Therefore, HSQC experiments of heparin acquired with a sufficient number of scans allow detection of a small peak at 5.20/93.4 ppm belonging to a reducing N-acetylglucosamine (FIG. 6A). Potassium permanganate oxidation of UFH lot 2 caused disappearance of the a reducing N-acetylglucosamine signal and appearance of cross peaks at 4.37/58.9 ppm and 3.88/81.8 ppm (FIG. 15). This result demonstrates that, similar to the situation for PI-HSNAc, potassium permanganate oxidation of unfractionated heparin results in the formation of an N-acetylglucosaminic acid residue at the reducing end of the chain.

Experiments were also conducted to show that certain peaks in the N-acetyl region can result from different chemical processing steps of heparin. For example, periodate oxidized heparin was submitted to acidic treatment. The treatment on an oxidized heparin preparation with an acid resulted in an increase of a peak at 2.08 ppm (FIG. 9). Some minor peaks in the 2.10 ppm region were also observed.

These experiments described above show that the peak at 2.10 ppm in the $^1$H 1D-NMR spectra of heparin is not OSCS and instead is a characteristic structural signature that is reflective of an oxidative processing step in the manufacture of unfractionated heparin. Based upon the experiments described above, the scheme provided likely results in structures A and B of FIG. 16. Oxidation agents, such as KMnO$_4$, react with the reducing N-acetyl glucosamine moieties to generate a modified N-acetylglucosaminic acid residue (Structure A) at the reducing end of the heparin chain. In this situation, the newly formed signal at 4.37 ppm/58.9 ppm in the HSQC spectrum can be assigned to the proton at the C2 position of the newly generated N-acetylglucosaminic acid. It is also possible that further oxidation of this structure may occur, resulting in the formation of a dicarboxylic acid (Structure B), however no confirmation of this structure is provided at present. This scheme (FIG. 16), also explains why the appearance of the signal at 2.10 ppm in the $_1$H-NMR spectrum is dependent on the presence of reducing end N-acetylglucosamine. Finally, since the formation of these structures results from oxidation conditions, we anticipate that other oxidation conditions, beyond potassium permanganate, could also potentially result in the formation of such structures.

In conclusion, it was found that oxidation conditions result in the conversion of N-acetylglucosamine residues at the reducing end of heparin chains to an N-acetylglucosaminic acid which yields a characteristic signal at 2.10 ppm in the $_1$H-NMR spectrum of the heparin. Therefore, this signal does not arise from an impurity or contaminant present within heparin, but rather represents a part of the heparin chain itself.

The references, patents and patent applications cited herein are incorporated by reference. Modifications and variations of these methods and products thereof will be obvious to those skilled in the art from the foregoing detailed description and are intended to be encompassed within the scope of the appended claims.

What is claimed:

1. A method of producing a heparin sample, comprising:
    performing a separation process on a heparin sample to determine if a structural signature of one or more of:

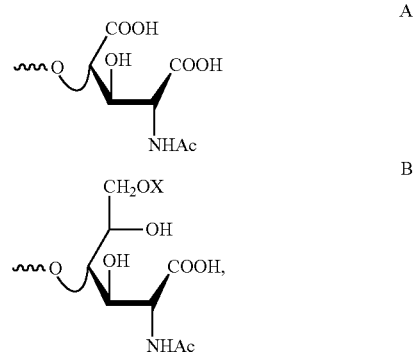

wherein in structure B, X=H or SO$_3$, is absent from or present in the heparin sample, wherein the presence of the structural signature indicates that the heparin sample was made by a method that includes oxidation or oxidation followed by treatment with an acid; and the absence of the structural signature indicates that the heparin sample was not made by the method; and
    if the heparin sample was made by the method, performing a step, wherein the step is one or more of classifying, selecting, accepting, discarding, releasing, withholding, processing into a drug product, shipping, formulating, labeling, packaging, releasing into commerce, selling, and offering for sale the heparin sample.

2. The method of claim 1, wherein the heparin sample is an unfractionated heparin sample or low molecular weight heparin (LMWH) sample.

3. The method of claim 1, wherein the step is to select, process into a drug product, formulate, or label, the heparin sample.

4. The method of claim 1, wherein the heparin sample is an unfractionated heparin sample and the step includes further processing the unfractionated heparin sample to produce a LMWH sample.

5. The method of claim 1, wherein the heparin sample is a LMWH sample and the step includes selecting, processing into a drug product, formulating, or labeling the LMWH sample.

6. The method of claim 1, wherein the heparin sample is an unfractionated heparin sample and the processing into drug product includes depolymerizing the unfractionated heparin sample to produce a LMWH sample.

7. The method of claim 1, wherein the method further comprises determining the amount of the structural signature present in the heparin sample.

8. The method of claim 1, wherein the presence of the structural signature

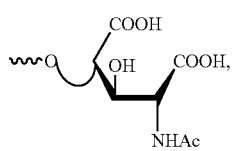

indicates that the heparin sample was made by a method that includes oxidation.

9. The method of claim 1, wherein the presence of the structural signature of one or more of:

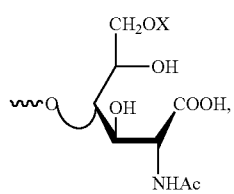

wherein in structure B, X=H or $SO_3$, indicates that the heparin sample was made by a method that includes oxidation followed by treatment with an acid.

10. The method of claim 1, wherein the separation process to determine the absence or presence of the structural signature is one of more of high performance liquid chromatography (HPLC), nuclear magnetic resonance (NMR), capillary electrophoresis (CE) and mass spectroscopy, and fast protein liquid chromatography (FPLC).

11. The method of claim 10, wherein the mass spectroscopy method is one or more of matrix-assisted laser desorption ionization-mass spectroscopy (MALDI-MS) or electrospray ionization-mass spectroscopy (ESI-MS).

12. A method of making a heparin sample, comprising:
performing a separation process on a heparin sample to determine the absence or presence of a structural signature in the heparin sample of one or more of:

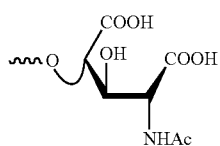

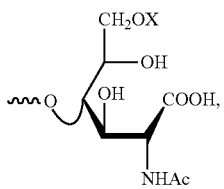

wherein in structure B, X=H or $SO_3$, and
determining if the heparin sample was made by a method that includes oxidation or oxidation followed by treatment with an acid, wherein the presence of the structural signature indicates that the heparin sample was made by the method and the absence of the structural signature indicates that that the heparin sample was not made by the method; and
if the heparin sample was made by the method, performing a step, of selecting processing into a drug product, formulating, or labeling the heparin sample.

13. The method of claim 12, wherein the heparin sample is an unfractionated heparin sample or low molecular weight heparin (LMWH) sample.

14. A method of making a heparin sample, comprising:
performing nuclear magnetic resonance (NMR) on a heparin sample to determine the absence or presence of a structural signature in the heparin sample of one or more of:

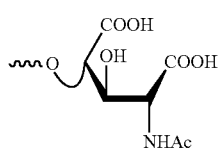

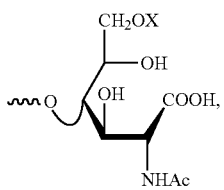

wherein in structure B, X=H or $SO_3$, and
determining if the heparin sample was made by a method that includes oxidation or oxidation followed by treatment with an acid, wherein the presence of the structural signature indicates that the heparin sample was made by the method and the absence of the structural signature indicates that the heparin sample was not made by the method; and
performing a step, of selecting, processing into a drug product, formulating, or labeling the heparin sample if the heparin sample was made by the method.

15. A method of assessing if a heparin sample is at risk for coloration, comprising:
performing a separation process on a heparin sample to determine if a structural signature of one or more of:

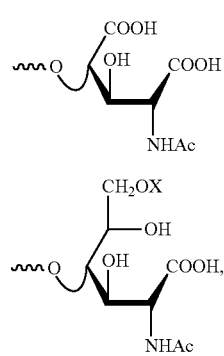

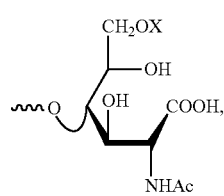

wherein in structure B, X=H or $SO_3$, is absent from or present in the heparin sample wherein the presence of the structural signature indicates that the heparin sample is not at risk for coloration and the absence of the structural signature indicates that that the heparin sample is at risk for coloration; and performing a step, of selecting, processing into a drug product, formulating, or labeling the heparin sample, if the heparin sample was made by the method.

* * * * *